United States Patent
Tsuda et al.

[19]

[11] Patent Number: 6,005,965
[45] Date of Patent: Dec. 21, 1999

[54] INSPECTION APPARATUS FOR SEMICONDUCTOR PACKAGES

[75] Inventors: Yukihiro Tsuda, Isehara; Takashi Kurihara, Naka-gun; Takahiro Ueda, Kawasaki; Tomikazu Tanuki, Hiratsuka; Yasuyoshi Suzuki, Fujisawa, all of Japan

[73] Assignee: Komatsu Ltd., Japan

[21] Appl. No.: 09/056,234

[22] Filed: Apr. 7, 1998

[30] Foreign Application Priority Data

Apr. 7, 1997 [JP] Japan ................................. 9-088237

[51] Int. Cl.⁶ ...................................................... G06K 9/00
[52] U.S. Cl. ...................... 382/145; 382/260; 250/559.08
[58] Field of Search ................................. 382/141, 144, 382/145, 146, 147, 148, 149, 150, 151, 260; 348/86, 87, 92, 125, 126; 364/468.01, 468.02; 356/390, 394, 398; 250/559.08, 559.34

[56] References Cited

U.S. PATENT DOCUMENTS 5,039,868  8/1991  Kobayashi et al. ............... 250/559.08
5,578,818  11/1996  Kain et al. ............................ 250/234
5,859,924  1/1999  Liu et al. ............................. 382/145

*Primary Examiner*—Joseph Mancuso
*Assistant Examiner*—V. Bali
*Attorney, Agent, or Firm*—Greer, Burns & Crain, Ltd.

[57] ABSTRACT

A semiconductor package inspection apparatus which varies the emission spectrum of an oblique imaging illumination and a plan view imaging illumination from each other, and which comprises a first filter which is provided on the optical path from a semiconductor package to an oblique imaging device, and which passes light from the oblique imaging illumination and blocks light from the plan view imaging illumination; a second filter which is provided on the optical path from a semiconductor package to the plan view imaging device, and which passes light from the plan view imaging illumination and blocks light from the oblique imaging illumination; and a control unit which simultaneously turns on the oblique imaging and plan view imaging illumination, and inspects terminals of the semiconductor package based on image data of the oblique imaging device and plan view imaging device.

19 Claims, 16 Drawing Sheets

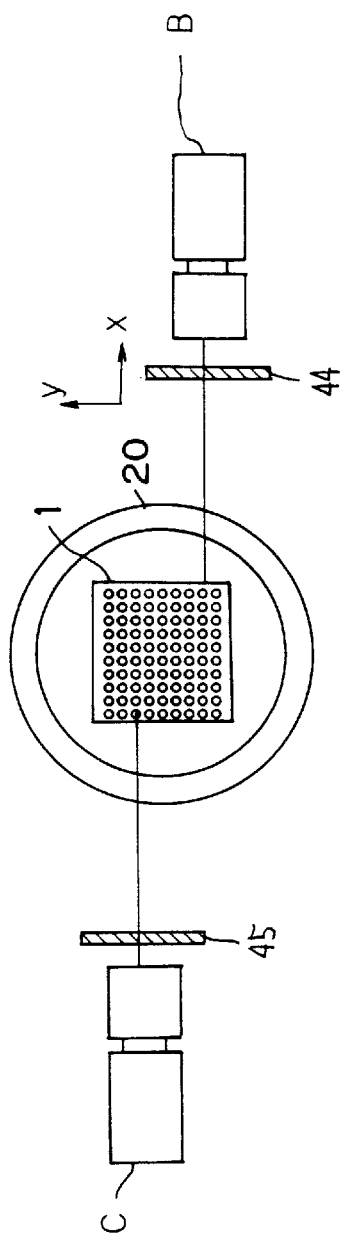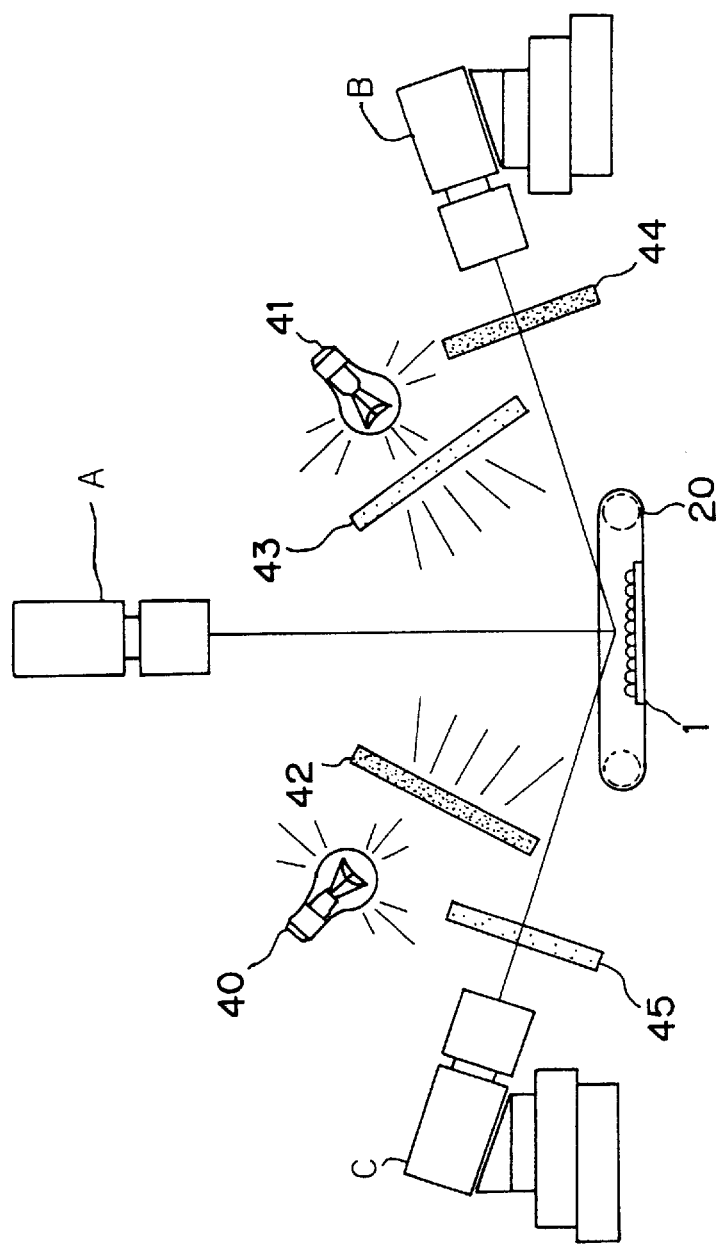
FIG.5(a)
FIG.5(b)

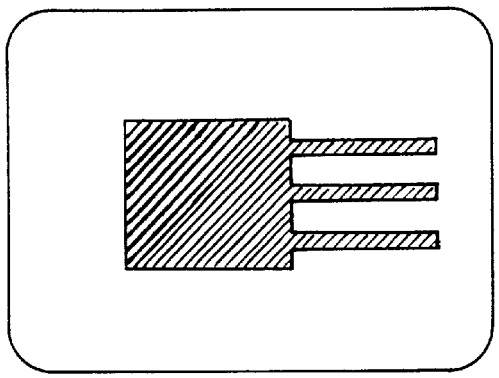 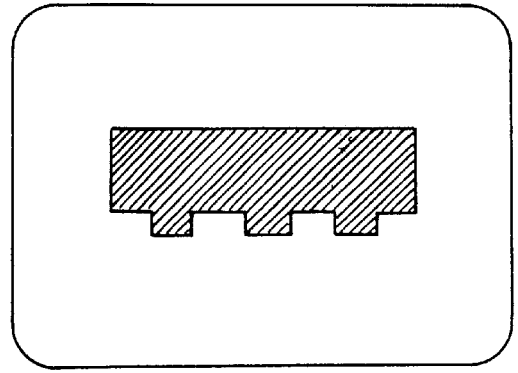
FIG.11(a)     FIG.11(b)

INSPECTION APPARATUS FOR SEMICONDUCTOR PACKAGES

BACKGROUND OF THE INVENTION

1. Field of the Invention

The present invention relates to a semiconductor package terminal inspection apparatus, which inspects PGA, CSP, BGA, QFP, QFJ and a variety of other semiconductor packages for various items such as displacement, pitch, flatness and tip uniformity of the terminals, missing letters, blurredness and displacement of markings indicated (e.g., stamped) on the surfaces of semiconductor packages, and voids inside semiconductor package surfaces.

2. Description of the Related Art

A semiconductor package called a Ball Grid Array (BGA) or Chip Size Package (CSP) (hereafter referred to jointly as BGA), features a 2-dimensional array of ball-shaped solder bumps on the underside surface of the semiconductor package. A BGA is installed on a printed circuit board in such a way that these solder bumps are soldered directly to the printed circuit board.

Conventionally, the inspection of various items such as displacement, pitch and flatness of the terminals in semiconductor packages of the type which the terminals are formed on the underside surface of the package as with BGA, was performed by means of a laser displacement measuring instrument which measures the distance to an inspection object using a triangulation principle.

With the abovementioned conventional technique, a laser displacement measuring instrument is positioned over the semiconductor package, which is arranged with the underside surface up, and the height of each solder bump was measured by using this laser displacement measuring instrument to scan one-by-one the vicinity of the top of each solder bump of the semiconductor package.

In conventional techniques that use a laser displacement measuring instrument, since the laser displacement measuring instrument measures the height of each solder bump one-by-one, inspection takes a long time, and if there is a scratch or the like on the surface of a solder bump, accurate inspection measurements cannot be achieved.

The specification of Japanese patent application No.8-124953 discloses a technique to solve the above-described problems. FIG. 8 shows the configuration of the apparatus according to this technique.

In FIG. 8, a BGA 1 is turned upside-down and placed on top of a BGA tray 3, a half mirror 4 is positioned over top of the BGA 1, and an illumination 5 for a camera A is positioned thereabove. Camera A images a plan view of the underside surface of BGA 1 via half mirror 4. An illumination 6 for a camera B is set up to the side of BGA 1, and camera B images, obliquely from above, the underside surface of BGA 1 where the balls (solder bumps) 2 are arrayed.

In the technology depicted in the FIG. 8, 3-dimensional information (plan location (x-y locations) and height (z location)) on each ball is obtained based on image data picked up by two cameras A, B. However, optimal imaging is not possible with each camera A, B when both illuminations 5, 6 are on at the same time. Therefore, it is required that, when imaging with camera A, only camera A illumination 5 is turned on, and when imaging with camera B, only camera B illumination 6 is turned on.

Thus, with the technology depicted in the FIG. 8, two cameras A, B must be operated alternately. Therefore, imaging takes time, and efficient inspection cannot be achieved.

Furthermore, when BGA with large dimensions is inspected or when high resolution is required, the image area of BGA is too large compared with the field of view of a camera. Therefore, in order to image BGA with a single imaging operation, two or more cameras must be installed. However, because BGA is smaller than the cameras, when these two cameras are set up side by side and imaging of the BGA is attempted, interference occurs between the cameras.

Furthermore, in addition to the inspection of the leads (terminals), semiconductor package inspections include the inspections for missing letters, blurredness and displacement of the markings (such as manufacturer's name and manufacturing number) indicated onto the upper surface of a package, and inspected for defects, such as voids occurring in a package. During these inspections as well, a camera and illumination are used in the same way as described above.

Because the optimal positioning of the illumination for these inspections differs from the illumination position for lead inspection, these inspections had to be performed separately from the lead inspection.

SUMMARY OF THE INVENTION

With the foregoing in view, it is an object of the present invention to provide a semiconductor package inspection apparatus, which achieves illumination that enhances inspection speed and inspection accuracy.

The first aspect of the present invention is a semiconductor package inspection apparatus, comprising oblique imaging means which images a package surface of a semiconductor package from an oblique direction at a prescribed angle of elevation; plan view imaging means which images a plan view image of the package surface of the semiconductor package; oblique imaging illumination means which illuminates the package surface for imaging by the oblique imaging means; and plan view imaging illumination means which illuminates the package surface for imaging by the plan view imaging means, whereby terminals of the semiconductor package are inspected based on image data of the oblique imaging means and the plan view imaging means, the inspection apparatus being characterized in that emission spectrum characteristics of the oblique imaging illumination means and plan view imaging illumination means are different from each other, and the inspection apparatus further comprises first filter means which is provided on the optical path from the semiconductor package to the oblique imaging means, and which passes light from the oblique imaging illumination means, and blocks light from the plan view imaging illumination means; second filter means which is provided on the optical path from the semiconductor package to the plan view imaging means, and which passes light from the plan view imaging illumination means, and blocks light from the oblique imaging illumination means; and control means which simultaneously turns on the oblique imaging and plan view imaging illumination means, and inspects the terminals of the semiconductor package based on image data of the oblique imaging means and plan view imaging means.

In accordance with the first aspect of the present invention, because the emission spectrum characteristics of the oblique imaging illumination means and plan view imaging illumination means are varied, turning on both of these illumination means at the same time enables simultaneous imaging by the oblique imaging means and the plan view imaging means. This enables imaging time to be shortened, and makes possible efficient semiconductor inspection.

The second aspect of the present invention is a semiconductor package inspection apparatus, comprising oblique imaging means which images a package surface of a semiconductor package from an oblique direction at a prescribed angle of elevation; plan view imaging means which images a plan view image of the package surface of the semiconductor package; oblique imaging illumination means which illuminates the package surface for imaging by the oblique imaging means; and plan view imaging illumination means which illuminates the package surface for imaging by the plan view imaging means, whereby terminals of the semiconductor package are inspected based on image data of the oblique imaging means and the plan view imaging means, the semiconductor package inspection apparatus being characterized in that polarization characteristics of the oblique imaging illumination means and plan view imaging illumination means are different from each other, and the semiconductor package inspection apparatus further comprises first polarizing filter means which is provided on the optical path from the semiconductor package to the oblique imaging means, and which passes light from the oblique imaging illumination means, and blocks light from the plan view imaging illumination means; second polarizing filter means which is provided on the optical path from the semiconductor package to the plan view imaging means, and which passes light from the plan view imaging illumination means, and blocks light from the oblique imaging illumination means; and control means which simultaneously turns on the oblique imaging and plan view imaging illumination means, and inspects terminals of the semiconductor package based on image data of the oblique imaging means and plan view imaging means.

In accordance with the second aspect of the present invention, because the polarization characteristics of the oblique imaging illumination means and plan view imaging illumination means are varied, turning on both of these illumination means at the same time enables simultaneous imaging by the oblique imaging means and the plan view imaging means. This enables imaging time to be shortened, and makes possible efficient semiconductor inspection.

The third aspect of the present invention is a semiconductor package inspection apparatus, comprising oblique imaging means which images a package surface of a semiconductor package from an oblique direction at a prescribed angle of elevation; plan view imaging means which images a plan view image of the package surface of the semiconductor package; oblique imaging illumination means which illuminates the package surface for imaging by the oblique imaging means; and plan view imaging illumination means which illuminates the package surface for imaging by the plan view imaging means, whereby terminals of the semiconductor package are inspected based on image data of the oblique imaging means and the plan view imaging means, the semiconductor package inspection apparatus being characterized in that the oblique imaging means comprises a first oblique imaging means which is positioned on one side of the semiconductor package, and a second oblique imaging means which is positioned on the opposite side of the semiconductor package from this first oblique imaging means, and these first and second oblique imaging means are positioned by shifting the optical axis of each imaging means so that a different area of the semiconductor package is imaged by each; and the oblique imaging illumination means comprises a first oblique imaging illumination means which illuminates the package surface for imaging by the first oblique imaging means, and a second oblique imaging illumination means which illuminates the package surface for imaging by the second oblique imaging means, and the respective emission spectrum characteristics of these first and second oblique imaging illumination means and the plan view imaging illumination means are different from each other, and the inspection apparatus further comprises first filter means which is provided on the optical path from the semiconductor package to the first oblique imaging means, and which passes light from the first oblique imaging illumination means, and blocks light from the plan view imaging illumination means and the second oblique imaging illumination means; second filter means which is provided on the optical path from the semiconductor package to the second oblique imaging means, and which passes light from the second oblique imaging illumination means, and blocks light from the first oblique imaging illumination means and the plan view imaging illumination means; third filter means which is provided on the optical path from the semiconductor package to the plan view imaging means, and which passes light from the plan view imaging illumination means, and blocks light from the first and second oblique imaging illumination means; and control means which simultaneously turns on the first and second oblique imaging illumination means and the plan view imaging illumination means, and inspects the terminals of the semiconductor package based on image data of the first and second oblique imaging means and plan view imaging means.

In accordance with the third aspect of the present invention, separate illumination means are installed for each of the first and second oblique imaging means set up on both sides of a semiconductor package so as to sandwich it between them, and for the plan view imaging means, and varying the emission spectrum characteristics of each of these various illumination means, and turning each of these illumination means on at the same time, enables simultaneous imaging by the first and second oblique imaging means and plan view imaging means. Therefore, it enables the enlargement of the simultaneous imaging area without causing these two imaging means to interfere with one another, and is effective when inspecting BGA with large dimensions, and when high resolution is required.

The fourth aspect of the present invention is a semiconductor package inspection apparatus, comprising oblique imaging means which images a package surface of a semiconductor package from an oblique direction at a prescribed angle of elevation; plan view imaging means which images a plan view image of the package surface of the semiconductor package; oblique imaging illumination means which illuminates the package surface for imaging by the oblique imaging means; and plan view imaging illumination means which illuminates the package surface for imaging by the plan view imaging means, whereby terminals of the semiconductor package are inspected based on image data of these oblique imaging means and plan view imaging means; the inspection apparatus being characterized in that the oblique imaging means comprises a first oblique imaging means which is positioned on one side of the semiconductor package, and a second oblique imaging means which is positioned on the opposite side of the semiconductor package from this first oblique imaging means, and these first and second oblique imaging means are positioned by shifting the optical axis of each imaging means so that a different area of the semiconductor package is imaged by each; and the oblique imaging illumination means comprises a first oblique imaging illumination means which illuminates the package surface for imaging by the first oblique imaging means, and a second oblique imaging illumination means which illuminates the package surface for imaging by the second oblique imaging means, and the respective polarization characteristics of these first and second oblique imaging illumination means are varied, and the inspection apparatus further comprises a first polarizing filter means which is provided on the optical path from the semiconductor package to the first oblique imaging means, and which passes light from the first oblique imaging illumination means, and blocks light from the second oblique imaging illumination means; second polarizing filter means which is provided on the optical path from the semiconductor package to the second oblique imaging means, and which passes light from the second oblique imaging illumination means, and blocks light from the first oblique imaging illumination means; and control means which turns on the first and second oblique imaging illumination means at the same time, controls each of the illumination means so that these first and second oblique imaging illumination means and the plan view imaging illumination means are on alternately, and inspects terminals of the semiconductor package based on image data of the first and second oblique imaging means and plan view imaging means.

In accordance with the present invention, separate illumination means are installed for each of the first and second oblique imaging means set up on both sides of a semiconductor package so as to sandwich it between them. Varying the polarization characteristics of each of these illumination means, and turning these illumination means on at the same time, enables simultaneous imaging by the first and second oblique imaging means. And enabling the first and second oblique imaging means to image different areas of the surface of the semiconductor package enlarges the simultaneously imaged area.

The fifth aspect of the present invention is a semiconductor package inspection apparatus, comprising oblique imaging means which images a package surface of a semiconductor package from an oblique direction at a prescribed angle of elevation; plan view imaging means which images a plan view image of the package surface of the semiconductor package; oblique imaging illumination means which illuminates the package surface for imaging by the oblique imaging means; plan view imaging illumination means which illuminates the package surface for imaging by the plan view imaging means, whereby terminals of the semiconductor package are inspected based on image data of these oblique imaging means and plan view imaging means, the inspection apparatus being characterized in that the oblique imaging means comprises a first oblique imaging means which is positioned on one side of the semiconductor package, and a second oblique imaging means which is positioned on the same side of the semiconductor package as this first oblique imaging means, and the optical axis of each imaging means is set so that these first and second oblique imaging means each image a different area of the semiconductor package; and the oblique imaging illumination means comprises a first oblique imaging illumination means which illuminates the package surface for imaging by the first oblique imaging means, and a second oblique imaging illumination means which illuminates the package surface for imaging by the second oblique imaging means, and the respective emission spectrum characteristics of these first and second oblique imaging illumination means and the plan view imaging illumination means are varied; and it is further characterized in that it comprises a dichroic beam splitter which is provided on the optical path from the semiconductor package to the first and second oblique imaging means, and which splits incident light so as to guide the light of the first oblique imaging illumination means to the first oblique imaging means, and to guide the light of the second oblique imaging illumination means to the second oblique imaging means; filter means which is provided on the optical path from the semiconductor package to the plan view imaging means, and which passes light from the plan view imaging illumination means, and blocks light from the first and second oblique imaging illumination means; and control means which simultaneously turns on the first and second oblique imaging illumination means and the plan view imaging illumination means, and inspects terminals of the semiconductor package based on image data of the first and second oblique imaging means and plan view imaging means.

In accordance with the fifth aspect of the present invention, positioning the first and second oblique imaging means on one side of the semiconductor package makes the apparatus more compact. Further, with this invention, separate illumination means are installed for each of the first and second oblique imaging means and the plan view imaging means, and varying the emission spectrum characteristics of each of these various illumination means, and turning each of these illumination means on at the same time, enables simultaneous imaging by the first and second oblique imaging means and plan view imaging means. And enabling the first and second oblique imaging means to image different areas of the surface of the semiconductor package enlarges the simultaneously imaged area. Further, this invention uses a dichroic beam splitter to split the optical path to the first and second oblique imaging means, thereby furnishing each oblique imaging means with double the amount of incident light possible with an ordinary beam splitter, and increasing the depth of focus of each of these oblique imaging means.

The sixth aspect of the present invention is a semiconductor package inspection apparatus, comprising oblique imaging means which images a package surface of a semiconductor package from an oblique direction at a prescribed angle of elevation; plan view imaging means which images a plan view image of the package surface of the semiconductor package; oblique imaging illumination means which illuminates the package surface for imaging by the oblique imaging means; and plan view imaging illumination means which illuminates the package surface for imaging by the plan view imaging means, whereby terminals of the semiconductor package are inspected based on image data of these oblique imaging means and plan view imaging means; the inspection apparatus being characterized in that the oblique imaging means comprises a first oblique imaging means which is positioned on one side of the semiconductor package, and a second oblique imaging means which is positioned on the same side of the semiconductor package as this first oblique imaging means, and the optical axis of each imaging means is set so that these first and second oblique imaging means each image a different area of the semiconductor package; and the oblique imaging illumination means comprises a first oblique imaging illumination means which illuminates the package surface for imaging by the first oblique imaging means, and a second oblique imaging illumination means which illuminates the package surface for imaging by the second oblique imaging means, and the respective polarization characteristics of these first and second oblique imaging illumination means are varied, and the inspection apparatus further comprises a polarized beam splitter which is provided on the optical path from the semiconductor package to the first and second oblique imaging means, and which splits incident light so as to guide the light from the first oblique imaging illumination means to the first oblique imaging means, and to guide the light from the second oblique imaging illumination means to the second oblique imaging means; and control means which simultaneously turns on the first and second oblique imaging illumination means, controls each of the illumination means so that these first and second oblique imaging illumination means and the plan view imaging illumination means are on alternately, and inspects terminals of the semiconductor package based on image data of the first and second oblique imaging means and plan view imaging means.

In accordance with the sixth aspect of the present invention, positioning the first and second oblique imaging means on one side of the semiconductor package makes the apparatus more compact. Further, with the present invention, separate illumination means are installed for each of the first and second oblique imaging means, and varying the polarization characteristics of each of these illumination means, and turning each of these illumination means on at the same time, enables simultaneous imaging by the first and second oblique imaging means. And enabling the first and second oblique imaging means to image different areas of the surface of the semiconductor package enlarges the simultaneously imaged area.

The seventh aspect of the present invention is a semiconductor package inspection apparatus, comprising first imaging means which images a package surface of a semiconductor package from a first direction; second imaging device which images the package surface of the semiconductor package from a second direction that differs from the first direction; first illumination means which illuminates the package surface for imaging by the first imaging means; and second illumination means which illuminates the package surface for imaging by the second imaging means, whereby the semiconductor package is inspected using these first and second image data, the inspection apparatus being characterized in that emission wavelength characteristics of the first and second illumination means are different from each other, and the inspection apparatus further comprises first filter means which is provided on the optical path from the semiconductor package to the first imaging means, and which passes light from the first illumination means, and blocks light from the second illumination means; second filter means which is provided on the optical path from the semiconductor package to the second imaging means, and which passes light from the second illumination means, and blocks light from the first illumination means; and control means which simultaneously turns on the first and second illumination means, and inspects the semiconductor package based on image data of the first and second imaging means.

In accordance with the present invention, because the emission spectrum characteristics of the first and second illumination means are varied, turning on both of these illumination means at the same time enables the first and second imaging means to image simultaneously. This enables imaging time to be shortened, and makes efficient semiconductor inspection possible.

The eighth aspect of the present invention is a semiconductor package inspection apparatus, comprising first imaging means which images a package surface of a semiconductor package from a first direction; second imaging device which images the package surface of the semiconductor package from a second direction that differs from the first direction; first illumination means which illuminates the package surface for imaging by the first imaging means; and second illumination means which illuminates the package surface for imaging by the second imaging means, whereby the semiconductor package is inspected using these first and second image data, the inspection apparatus being characterized in that polarization characteristics of the first and second illumination means are different from each other, and the inspection apparatus further comprises first polarizing filter means which is provided on the optical path from the semiconductor package to the first imaging means, and which passes light from the first illumination means, and blocks light from the second illumination means; second polarizing filter means which is provided on the optical path from the semiconductor package to the second imaging means, and which passes light from the second illumination means, and blocks light from the first illumination means; and control means which simultaneously turns on the first and second illumination means, and inspects the semiconductor package based on image data of the first and second imaging means.

In accordance with the eighth aspect of the present invention, because the polarization characteristics of the first and second illumination means are varied, turning on both of these illumination means at the same time enables the first and second imaging means to image simultaneously. This enables imaging time to be shortened, and makes efficient semiconductor inspection possible.

The ninth aspect of the present invention is a semiconductor package inspection apparatus having an imaging device for imaging an area including an upper surface of a semiconductor package which is provided with a plurality of metal terminals, for inspecting markings indicated onto the upper surface of the semiconductor package as well as the semiconductor package and the metal terminals based on image data from the imaging device, comprising illumination means which illuminates the area including the upper surface of the semiconductor package using linearly polarized light with a prescribed direction of polarization; a polarized beam splitter which is provided above the semiconductor package, and which splits into respectively different directions linearly polarized light with a direction of polarization coinciding with linearly polarized light from the illumination means and linearly polarized light with a direction of polarization being orthogonal to linearly polarized light from the illumination means, within the illuminated light from the illumination means reflected by the semiconductor package; first imaging means which is provided on one of the optical paths split by the polarized beam splitter, and on which is incident the linearly polarized light with a direction of polarization coinciding with the linearly polarized light from the illumination means; second imaging means which is provided on the other optical path split by the polarized beam splitter, and on which is incident the linearly polarized light with a direction of polarization being orthogonal to the linearly polarized lights from the illumination means; and control means which inspects the semiconductor package and metal terminals based on image data from the first imaging means, and inspects markings indicated on the upper surface of the semiconductor package based on image data from the second imaging means.

In accordance with the ninth aspect of the present invention, when a linearly polarized light with a prescribed direction of polarization is irradiated onto a semiconductor package, the reflected light from the metal terminals and upper surface of the semiconductor package, excluding the markings, is primarily just surface reflection, and the direction of polarization of this reflected light becomes the same linearly polarized light as the illuminated light. Conversely, because diffuse reflection occurs in the markings, this reflected light comprises both components, that is, a direction of polarization that is the same as that of the illuminated light, and a direction of polarization that differs exactly 90 degrees therefrom.

Therefore, if the polarized beam splitter splits the illuminated light into a component with a direction of polarization that is the same as the illuminated light, and a component with a direction of polarization that differs exactly 90 degrees therefrom, and these beams are guided separately to the respective imaging means, one of the imaging means can obtain clear images of the markings, while the other imaging means can obtain clear images of the metal terminals and upper surface of the semiconductor package (excluding the markings) alone.

Therefore, the present invention enables the simultaneous inspection of the markings, semiconductor package and metal terminals, makes it possible to obtain suitably clear images of each of these inspections, respectively and enhances the accuracy of each inspection.

The tenth aspect of the present invention is a semiconductor package inspection apparatus having an imaging device for imaging a semiconductor package which is provided with a plurality of metal terminals and is placed on an inspection table, for inspecting the metal terminals based on image data from the imaging device, the inspection apparatus being characterized in that surface of the inspection table which serves as a background to the metal terminals within a field of view region of the imaging device, exhibits diffuse reflection or absorption reflection properties, and the inspection apparatus further comprises illumination means which emits a linearly polarized light with a prescribed direction of polarization to illuminate the field of view region of the imaging device; and polarizing filter means which is provided between the imaging device and the semiconductor package, and which only passes polarized light with a direction of polarization being orthogonal to the linearly polarized light from the illumination means.

In accordance with the tenth aspect of the present invention, when a linearly polarized light with a prescribed direction of polarization is irradiated onto a semiconductor package, because the reflection from the metal terminals of the semiconductor package is mainly just surface reflection, the direction of polarization of that reflected light does not change. Conversely, because the surface of the inspection table that becomes the background for the metal terminals is surface coated so that diffuse reflection occurs, the direction of polarization of the reflected light from this inspection table inclines 90° relative to the direction of polarization of the illuminated light. Since the polarizing filter means is designed to pass only polarized light with a direction of polarization that is orthogonal to the linearly polarized light of the illumination means, only the reflected light from the inspection table is incident on the imaging means, and that portion of the semiconductor package corresponding to the metal terminals shows up as a shadow.

Thus, the present invention makes it possible to obtain images in which the metal terminals become dark shadows, and the background thereto appears bright. This makes it possible to achieve images that are practically equivalent to those imaged using backlighting, but without the use of backlighting.

BRIEF DESCRIPTION OF THE DRAWINGS

FIGS. 5(a) and 5(b) are schematic diagrams showing a fifth embodiment of the present invention;

FIGS. 11(a) and 11(b) are schematic diagrams showing examples of images picked up by the ninth embodiment of the present invention;

DESCRIPTION OF THE EMBODIMENTS

The embodiments of the present invention will be described with reference to the attached drawings.

In the following embodiments, semiconductor packages being inspected are BGA 1. As is well known, a BGA 1 is a land grid array (LGA) type chip carrier that uses a printed board, in which the upper surface of the chip is molded and a plurality of solder bumps (hereafter referred to as balls) is formed on the underside surface in a grid-like shape.

First Embodiment

Figure 1:
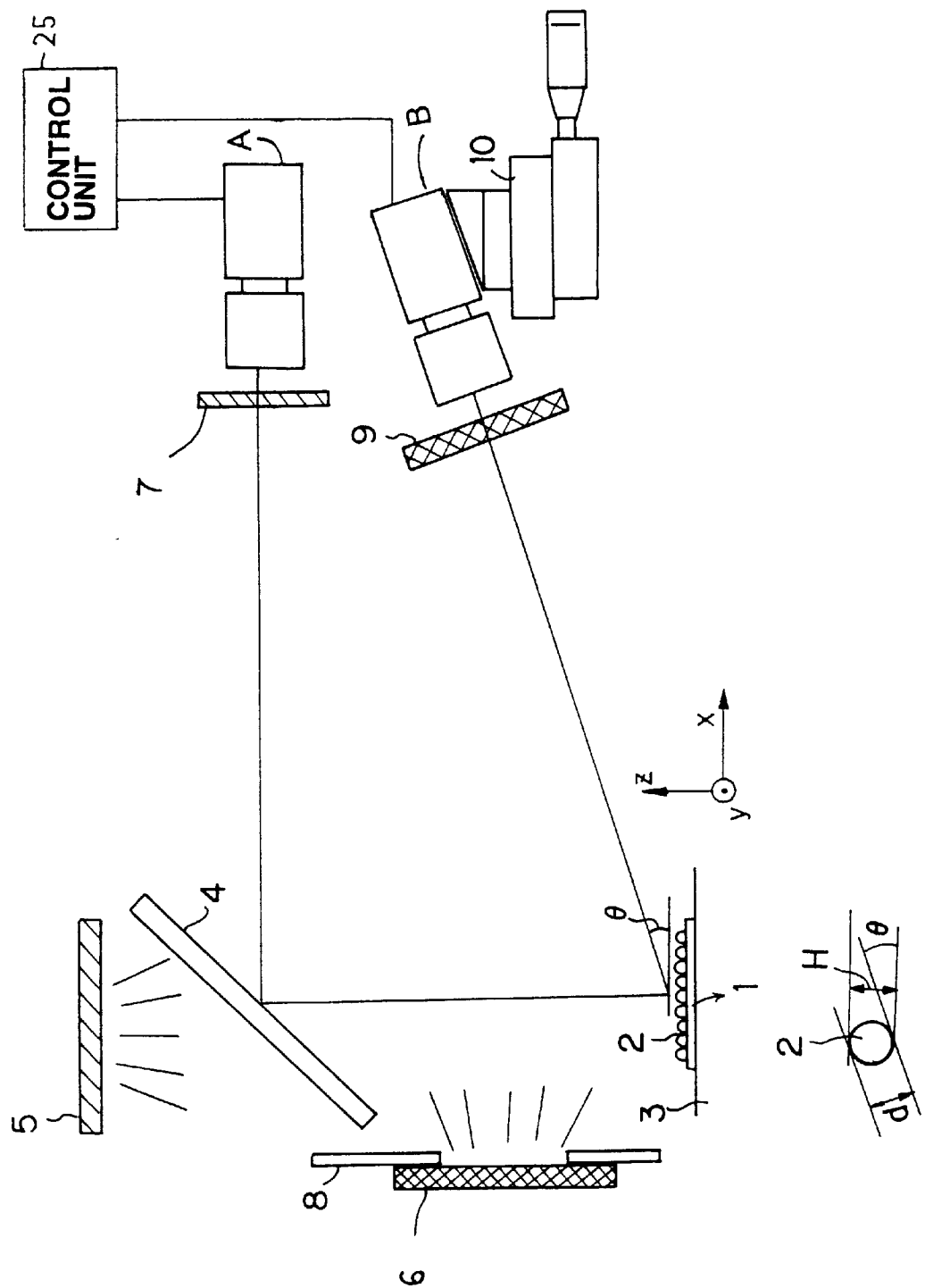
FIG. 1 is a schematic diagram showing a first embodiment of the present invention.

FIG. 1 shows a first embodiment of the present invention.

In FIG. 1, a BGA 1 is turned with the underside surface up and placed on a BGA tray 3 with the ball side, on which balls 2 are lined up in rows, facing up.

A half mirror 4 is positioned above the BGA 1, and thereabove is positioned a flat panel light 5, on which green light-emitting diodes (LED) are lined up in two-dimensional rows. Camera A images from directly overhead the underside surface of the BGA 1, where the balls 2 are located. In this case, camera A images the underside surface of the BGA 1 via a half mirror 4 as a plan view image. A green filter 7, which only passes green light, is positioned in front of camera A. This enables the image of the underside surface of BGA 1, which is illuminated by the green light 5, to be guided to camera A.

Meanwhile, a flat panel light 6, on which red LEDs are lined up in two-dimensional rows, is positioned to the side of BGA 1, and illumination regulating panels 8 are positioned in front of this flat panel light 6 to regulate the illumination area. In other words, the illumination regulating panels 8 are positioned to regulate the illumination area of light 6 to a region higher than a prescribed height from the upper surface of the BGA tray 3 so that the illumination from light 6 does not shine on the surface of the BGA 1 substrate.

Camera B images the underside surface of the BGA 1, on which the balls 2 are located, obliquely from above the BGA 1, and that angle of elevation θ is set at around 20 degrees, for instance. A red filter 9, which only passes red light, is positioned in front of camera B. This enables the image of the underside surface of BGA 1 illuminated by the red light 5 to be guided to camera B. An adjustment mechanism, which adjusts the position and direction of the camera is indicated by the number 10.

When a BGA inspection is implemented with this configuration, the control unit 25 turns on the green light 5 and the red light 6 at the same time.

Then, the control unit 25 causes camera A to image a plan view image of the underside surface of BGA 1, and determines the x-y locations of each of the balls 2 on the BGA 1 from this image data. Further, as needed, the control unit 25 also determines data on the diameter of each ball, and the presence of deformations.

Furthermore, simultaneously with camera A's imaging operation, the control unit 25 causes camera B to image the underside surface of BGA 1 obliquely from above, thereby determining the height d of each ball 2 in the oblique direction.

When it has obtained this height data d on each of the balls 2, the control unit 25 uses this height data d, together with a known ideal radius r of a ball and the angle of elevation θ of camera B to calculate the height H of each ball in the z direction using formula (1) below.

$$H = (d/\cos\theta) - (r/\cos\theta) + r \quad (1)$$

Thus, in accordance with this embodiment, a red light is used as the illumination for one camera, and a green light is used as the illumination for the other camera, the emission spectrums (in this case, the colors) of both lights are different, and an optical filter, which only passes one illumination light, is mounted in front of each camera A, B. This enables both lights 5, 6 to be on at the same time, thus enabling both cameras A, B to perform image processing simultaneously, which in turn enables BGA inspection processing to be carried out more rapidly than in the past.

Second Embodiment

Figure 2:
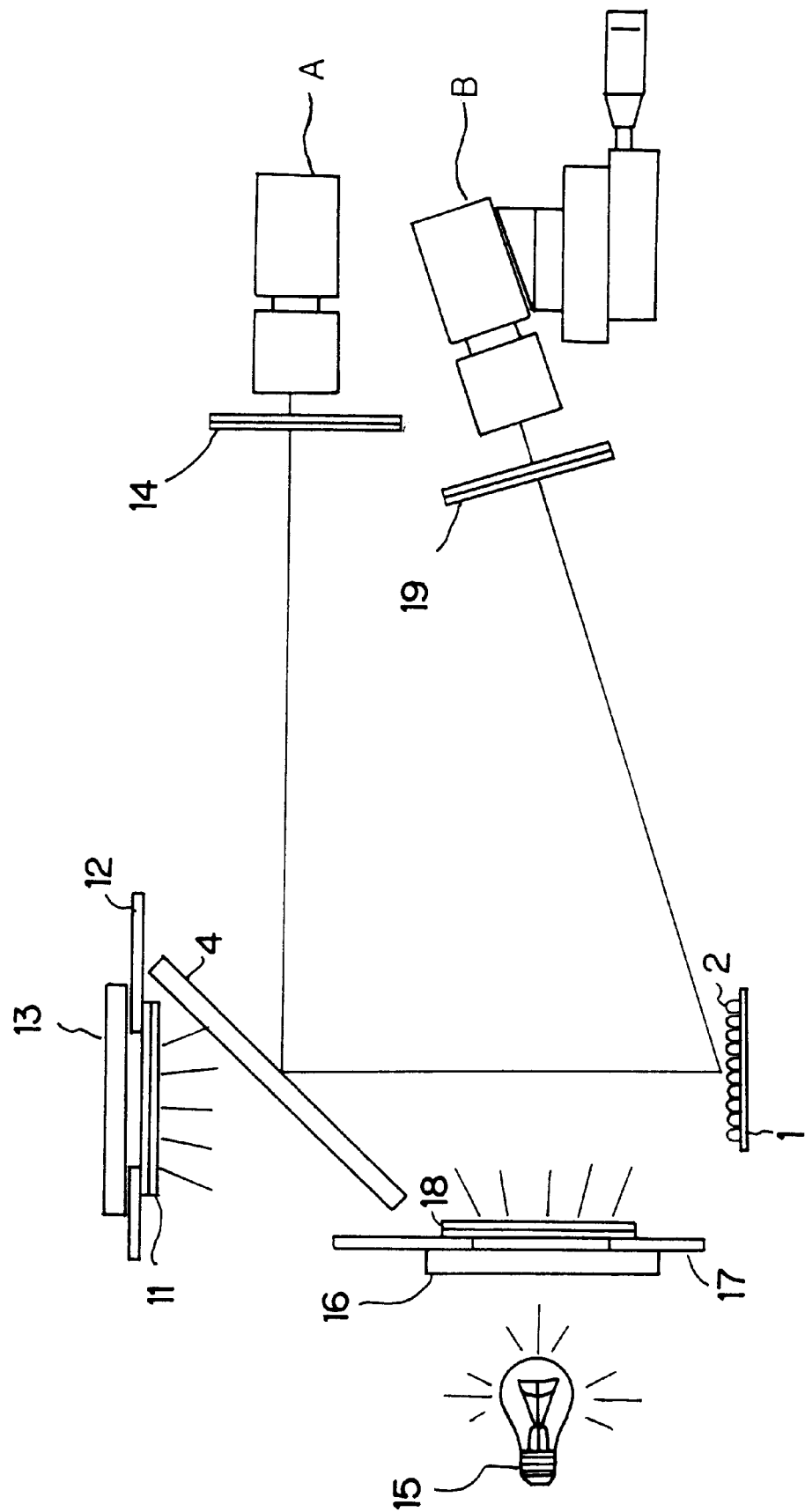
FIG. 2 is a schematic diagram showing a second embodiment of the present invention.

FIG. 2 shows a second embodiment of the present invention.

In this embodiment, a half mirror 4 is positioned above the BGA 1, and thereabove are positioned a polarizing panel 11, illumination regulating panels 12 and a flat panel light 13. A polarizing filter 14 is positioned in front of camera A.

A light 15 for camera B (in this case, a light bulb), a frosted glass or other homogenous lighting panel 16, illumination regulating panels 17 and a polarizing panel 18 are mounted to the side of BGA 1. A polarizing filter 19 is positioned in front of camera B.

In this configuration, the polarizing panel 11 for the camera A light, and the polarizing panel 18 for the camera B light are designed to vary by, for example, 90 degrees the direction of polarization of the light that has passed through them. The polarizing panel 11 for the camera A light only passes P polarized light within the illumination from light 13, and the polarizing panel 18 for the camera B light only passes S polarized light within the illumination from light 15. The polarizing filter 14 positioned in front of camera A only passes P polarized light, and the polarizing filter 19 positioned in front of camera B only passes S polarized light.

Therefore, according to the embodiment depicted in FIG. 2, the underside image of BGA 1 illuminated by light 13 can be guided to camera A, and the underside image of BGA 1 illuminated by light 15 can be guided to camera B. In other words, the BGA image resulting from light 13 does not reach camera B, and the BGA image resulting from light 15 does not reach camera A.

Thus, in the embodiment depicted in FIG. 2, because the direction of polarization of these two lights 13, 15 is varied (in this case, by 90 degrees) by the polarizing panels 11, 18, and the BGA image resulting from each light with its different direction of polarization is guided only to the corresponding camera by the polarizing filters 14, 19, both lights 13, 15 can be on at the same time, and both cameras A, B can carry out imaging simultaneously. This enables BGA inspection processing to be carried out more rapidly than in the past.

Third Embodiment

Figure 3:
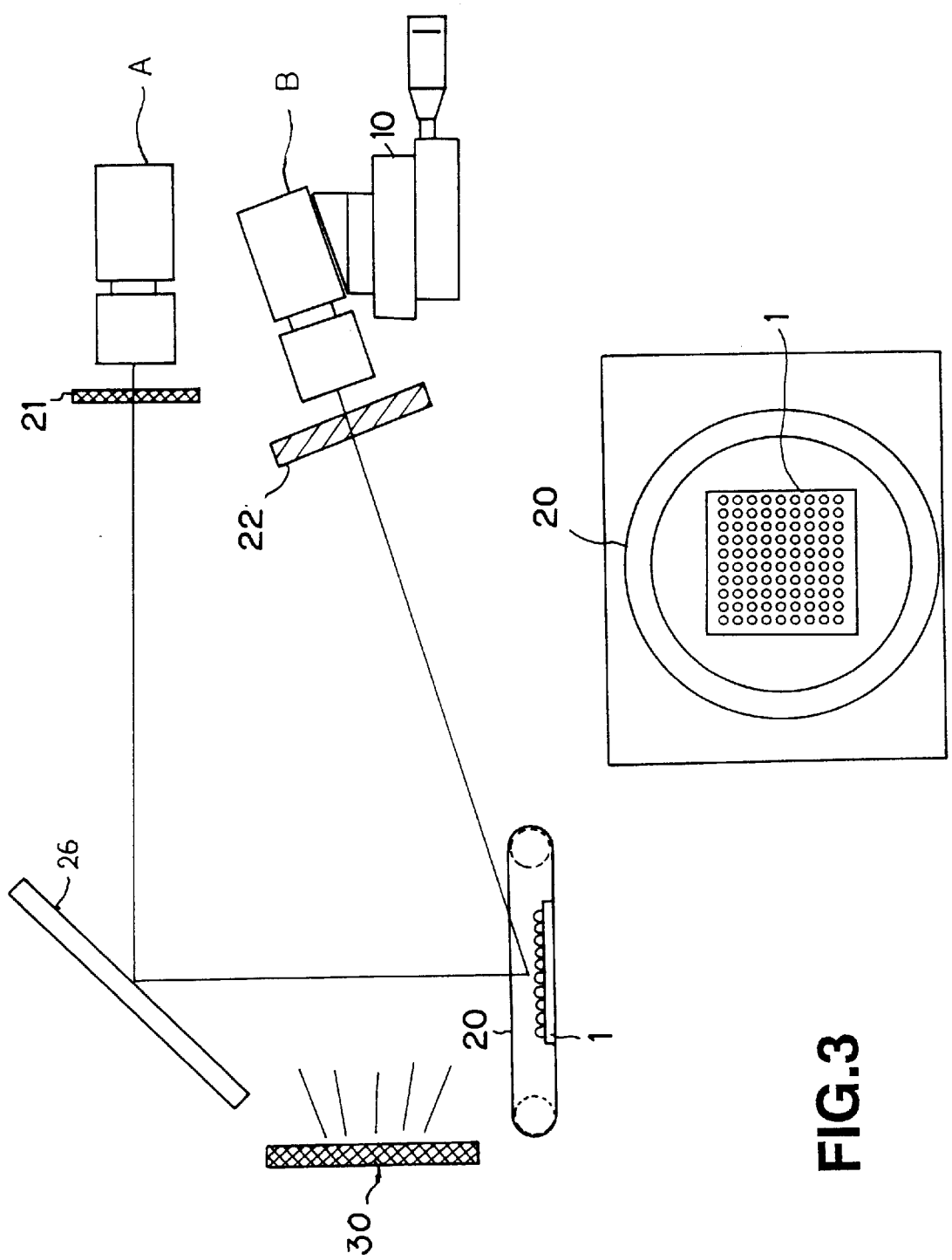
FIG. 3 is a schematic diagram showing a third embodiment of the present invention.

FIG. 3 shows a third embodiment of the present invention.

In this third embodiment, a ring-shaped fluorescent light 20 emitting blue light positioned so that it surrounds BGA 1 is used as the illumination for camera A. As illumination for camera B, a red LED 30 positioned to the side of BGA 1 is utilized.

An optical filter 21, which blocks red light but passes blue light, is positioned in front of camera A, and an optical filter 22, which blocks blue light but passes red light, is positioned in front of camera B.

In accordance with this configuration, the image of the underside surface of BGA 1 illuminated by the ring-shaped fluorescent light 20 is guided to camera A via a mirror 26, and the image of the underside surface of BGA 1 illuminated by the red LED 30 is guided to camera B.

In the third embodiment, because red light is used as the illumination for the one camera, and blue fluorescent light is used as the illumination for the other camera, and because an optical filter 21, 22, which only passes one of these lights, is mounted in front of each camera A, B, two lights 20, 30 can be on at the same time, and both cameras A, B can carry out imaging simultaneously, thus enabling BGA inspection processing to be carried out more rapidly than in the past.

In addition, in this embodiment, because the underside surface of BGA 1 is illuminated laterally for 360° by a ring-shaped fluorescent light 20, the entire underside surface of the BGA is uniformly illuminated, making it possible to achieve images with good contrast.

Fourth Embodiment

Figure 4A:
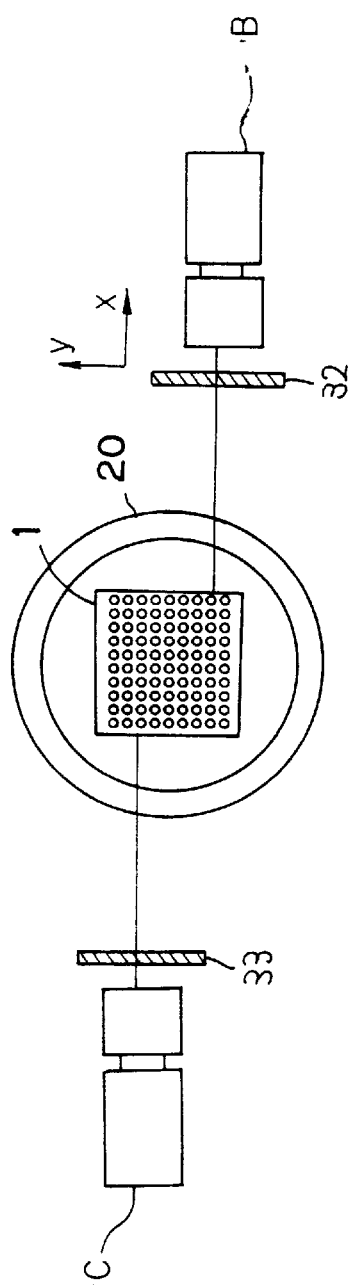
FIGS. 4(a) and 4(b) are schematic diagrams showing a fourth embodiment of the present invention.
Figure 4B:
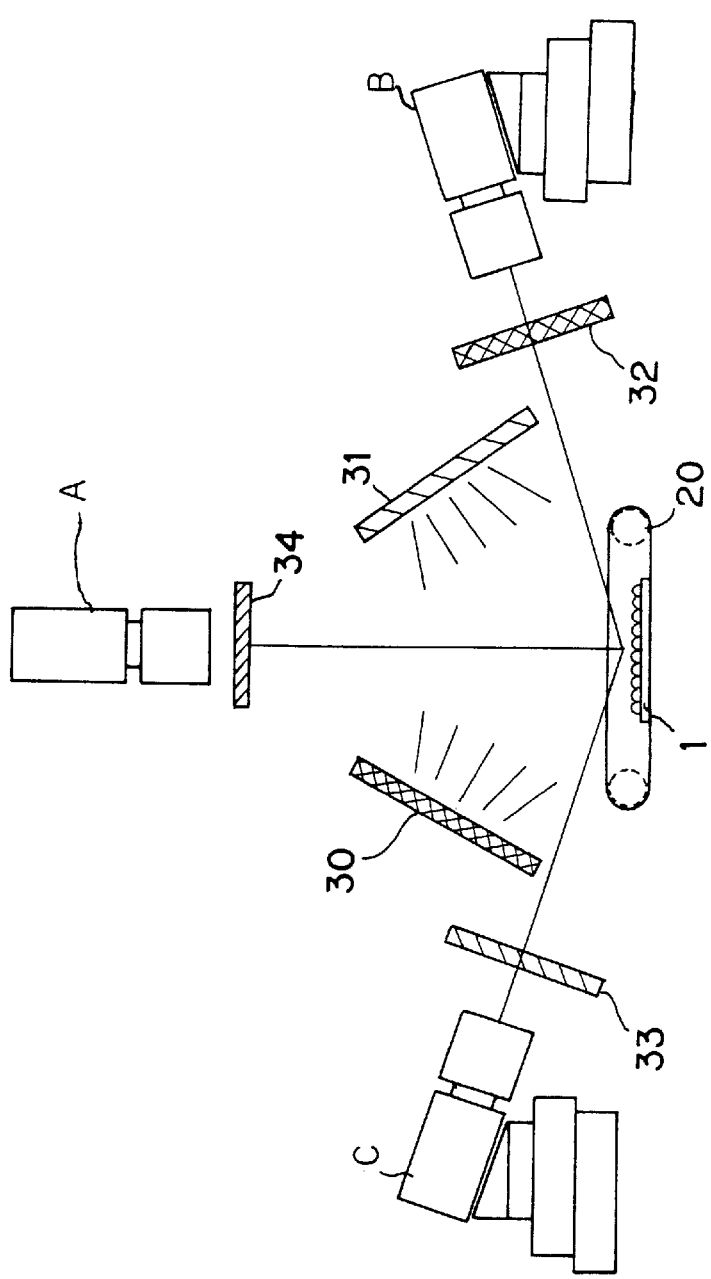

FIGS. 4(a) and 4(b) show fourth embodiment of the present invention.

FIG. 4(a) depicts a plan view, and FIG. 4(b) depicts a front view.

In this fourth embodiment, as the imaging equipment for obtaining ball height data, camera B and camera C are positioned so as to image the underside surface of a BGA 1 obliquely from above. Cameras B and C are mounted on either side of BGA 1, and the optical axis position of each camera is shifted in the y direction. In other words, camera B images half the area of the BGA 1 in the y direction, and camera C images the remaining half of the area.

The illumination for camera B, in this case, is a flat panel light 30 comprising red LEDs, and the illumination for camera C is a flat panel light 31 comprising green LEDs. A red filter 32, which only passes red light, is mounted in front of camera B, and a green filter 33, which only passes green light, is mounted in front of camera C.

Camera A is mounted above BGA 1 to image a plan view image of the underside surface of the BGA 1, and a ring-shaped blue fluorescent light 20 is positioned around the BGA 1 as the illumination for camera A. An optical filter 34, which blocks red and green light, and only passes blue light corresponding to the fluorescent light 20, is mounted in front of camera A.

In this fourth embodiment as well, these three lights 20, 30, 31 are on at the same time, and imaging operations can be carried out in parallel by the cameras A, B, C.

Thus, in accordance with this fourth embodiment, two cameras B, C are positioned on opposite sides of the BGA 1 to obtain ball height data by imaging the underside surface of the BGA 1 obliquely from above. Furthermore, the optical axis of each of these cameras B, C is shifted so that the field of view regions of camera B and C cover the entire area of the BGA 1. This enables the entire area of the BGA 1 to be covered by a single imaging without causing these two cameras B, C to interfere with one another, even when inspecting a large size BGA, and when high resolution is required.

Further, in this fourth embodiment, because the emission spectrums of each of the lights for these three cameras are varied, and because optical filters, which only pass corresponding light, are mounted in front of each of these cameras, these three lights 20, 30, 31 can be on at the same time, and imaging can be carried out simultaneously by these three cameras A, B, C, thus further speeding up BGA inspection processing.

Fifth Embodiment

FIGS. 5(a) and 5(b) show a fifth embodiment of the present invention.

FIG. 5(a) depicts a plan view, and FIG. 5(b) depicts a front view.

In this fifth embodiment, just as in the embodiment depicted in FIGS. 4(a) and 4(b) above, camera A is mounted above the BGA 1, and cameras B, C are positioned oblique to and above the BGA 1 on both sides, and the optical axis of each of these cameras B, C is shifted in the y direction. As the light source for camera A, a ring-shaped white fluorescent light 20 is mounted around this BGA 1 just as described above.

A light bulb 40 mounted oblique to and above the BGA 1 is used as the light source for camera B, and a light bulb 41 mounted oblique to and above the BGA 1 is used as the light source for camera C. A polarizing panel 42 is mounted in front of the illumination 40 for camera B, and a polarizing panel 43 is also mounted in front of the illumination 41 for camera C. The polarization angle of each polarizing panel 42, 43 is set so that the respective directions of polarization of the light passing through each of these polarizing panels 42, 43 is orthogonal. That is, when the light passing through polarizing panel 42 is P polarized light, the light passing through polarizing panel 43 is S polarized light.

Furthermore, a polarizing filter 44, which passes only polarized light that has passed through polarizing panel 42, and blocks polarized light that has passed through polarizing panel 43, is mounted in front of camera B, and a polarizing filter 45, which passes only polarized light that has passed through polarizing panel 43, and blocks polarized light that has passed through polarizing panel 42, is mounted in front of camera C.

In this fifth embodiment, two lights 40, 41 are on at the same time, but when these two lights 40, 41 are on, the white fluorescent light 20 is off. Further, when the white fluorescent light 20 is on, lights 40, 41 are off.

In other words, in this fifth embodiment, imaging with cameras B, C when lights 40, 41 are on is performed alternately with imaging by camera A when light 20 is on.

Sixth Embodiment

Figure 6:
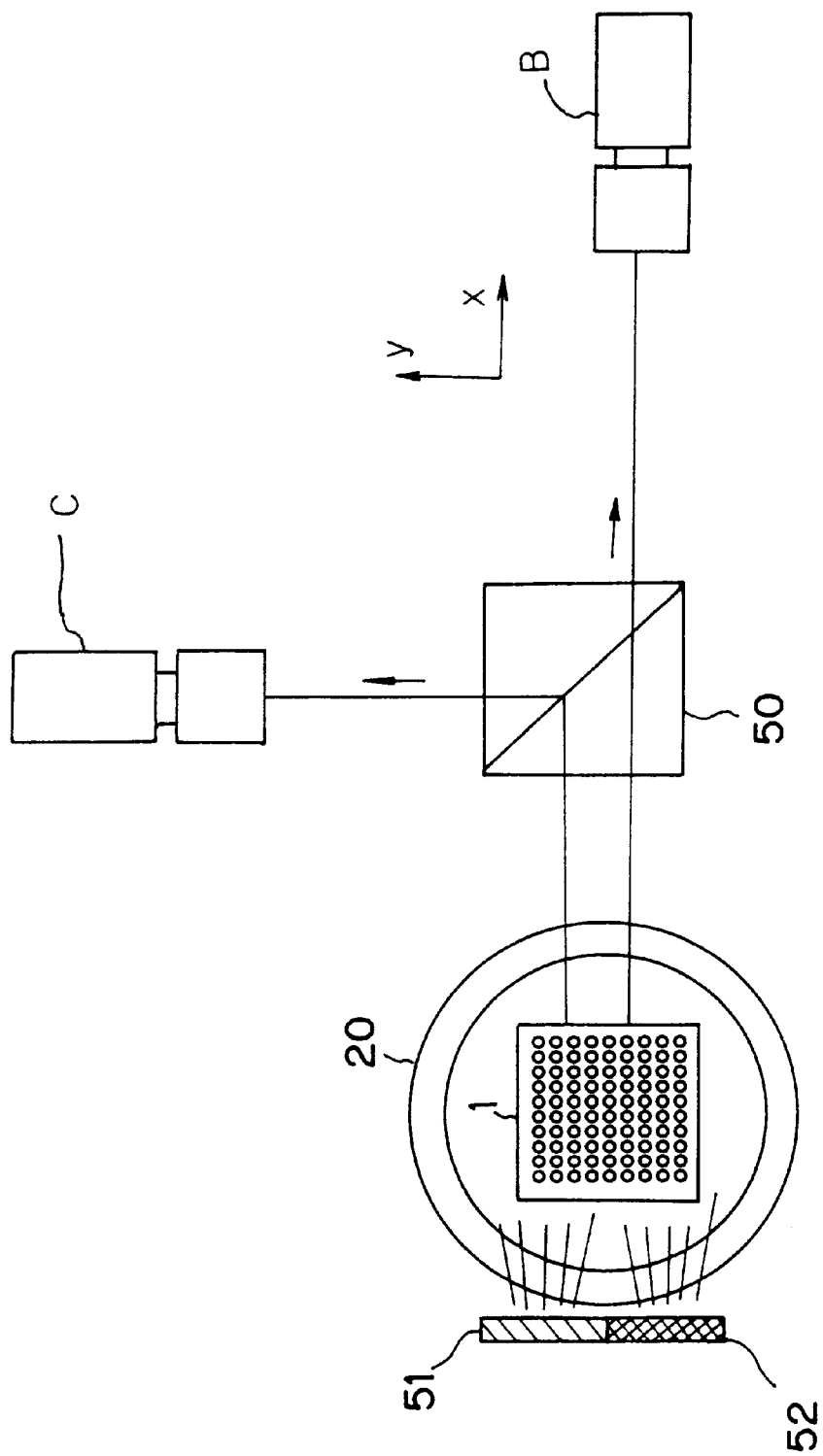
FIG. 6 is a schematic diagram showing a sixth embodiment of the present invention.

FIG. 6 shows a sixth embodiment of the present invention. FIG. 6 depicts a plan view looking at a BGA 1 from above.

In the fourth and fifth embodiments described above, cameras B, C were positioned on either side of the BGA 1. As a result, the apparatus for these embodiments is large.

Accordingly, this sixth embodiment attempts to make the apparatus smaller by positioning cameras B, C on one side of the BGA 1.

Just as in the embodiment depicted in FIGS. 4(a) and 4(b) above, a ring-shaped fluorescent light 20 is positioned around the BGA 1. Although not depicted in FIG. 6, just as in the embodiment depicted in FIGS. 4(a) and 4(b) above, camera A and an optical filter 34, which blocks red and green light, and passes only blue light corresponding to the fluorescent light 20, are positioned above the BGA 1.

On the left side of the BGA 1, a flat panel light 51, which comprises green LED for illuminating only the upper half of the BGA 1, and a flat panel light 52, which comprises red LED for illuminating only the bottom half of the BGA 1 are provided in proximity in a row arrangement.

Furthermore, mounted on the right side of the BGA 1 is a dichroic beam splitter 50, which possesses a spectral function, which deflects red incident light 90° and guides it to camera C, and passes red incident light as-is, and guides it to camera B. This dichroic beam splitter 50 can pass or deflect incident light in accordance with the wavelength of the incident light. Further, when it does so, it possesses a function which can ensure almost 1, without reducing by half the incoming/outgoing light ratio (amount of outgoing light/amount of incident (incoming) light), as happens with an ordinary beam splitter.

In accordance with this embodiment, just as in the embodiment depicted in FIGS. 4(a) and 4(b) above, three lights 20, 51, 52 are on at the same time, and imaging by cameras A, B, C is carried out in parallel.

In accordance with the sixth embodiment, because cameras B, C are positioned on one side of a BGA 1, the apparatus can be made more compact. Also, because a BGA light image with different wavelength spectrums is split by a dichroic beam splitter, the amount of incident light on cameras B, C is double that possible with an ordinary beam splitter. This enables the imaging of a bright BGA image with increased depth of focus, and enables enhanced inspection accuracy. In other words, if the amount of light incident on the camera is doubled, the camera aperture becomes smaller, and this increases the depth of focus.

Seventh Embodiment

Figure 7:
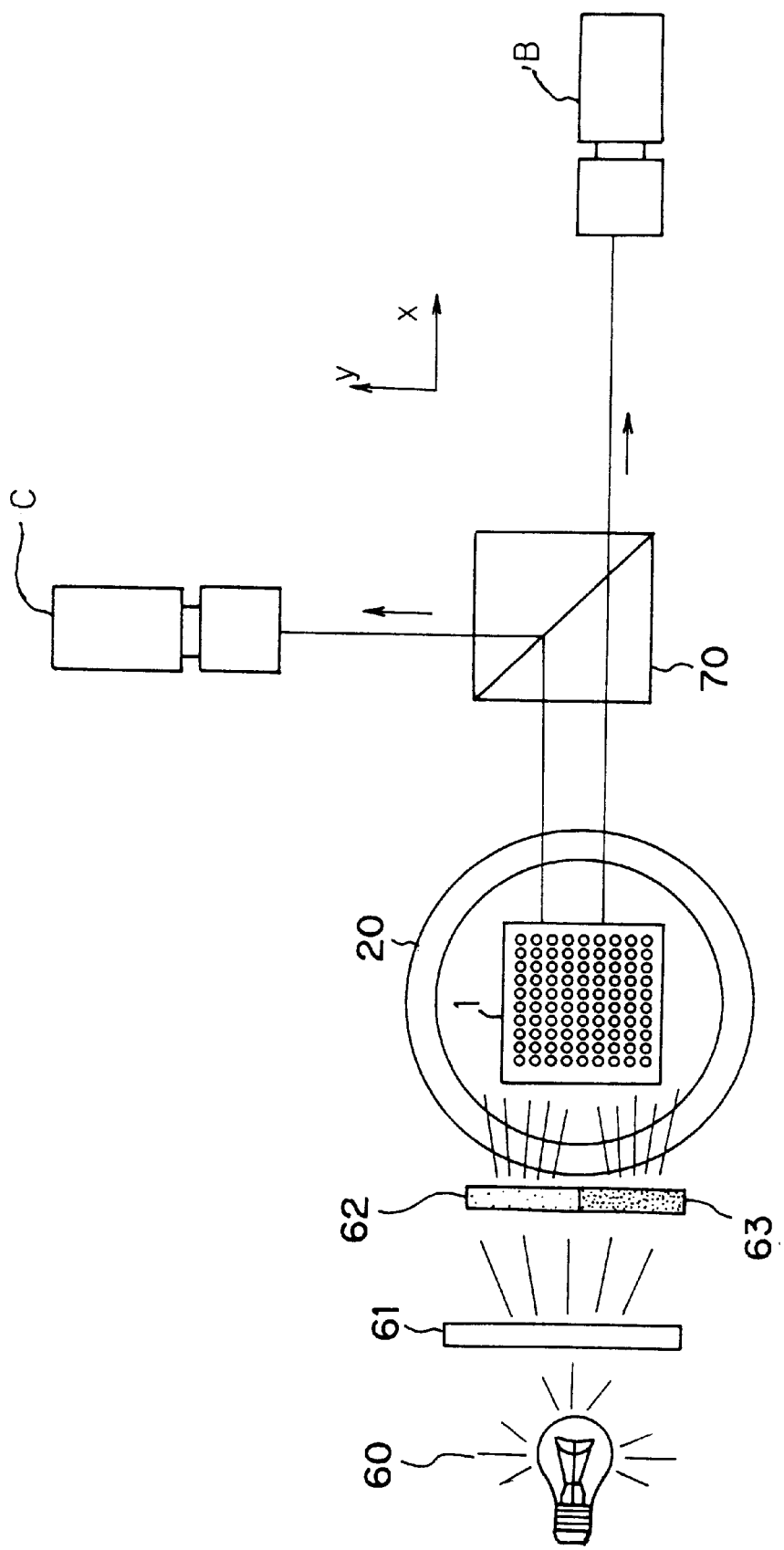
FIG. 7 is a schematic diagram showing a seventh embodiment of the present invention.
Figure 8:
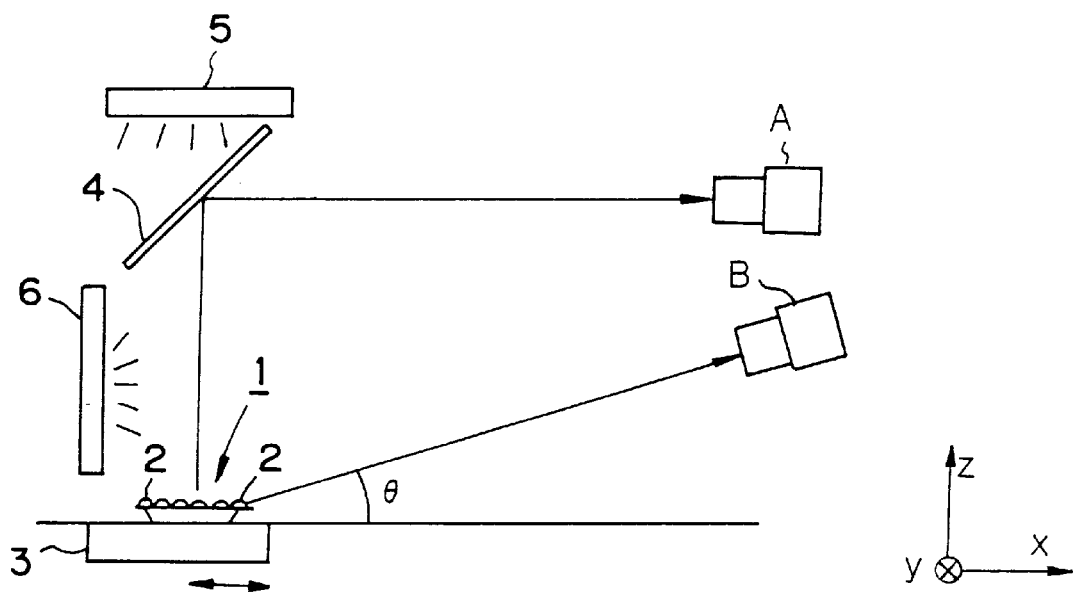
FIG. 8 is a schematic diagram showing a background technology of the present invention.

FIG. 7 shows a seventh embodiment of the present invention. FIG. 7 depicts a plan view looking at a BGA 1 from above.

Just as in the embodiment depicted in FIGS. 5(a) and 5(b) above, a ring-shaped fluorescent light 20 is positioned around the BGA 1. Although not depicted in FIG. 7, just as in the embodiment depicted in FIGS. 5(a) and 5(b) above, camera A is mounted above the BGA 1.

On the left side of the BGA 1 are mounted a light bulb 60 that serves as illumination for cameras B, C, an homogenous lighting panel 61, and polarizing panels 62 and 63.

Similar to the polarizing panels 42, 43 in the embodiment depicted in FIGS. 5(a) and 5(b) above, the polarization angle of polarizing panel 62 for illuminating only the upper half of the BGA 1, and the polarizing angle of polarizing panel 63 for illuminating only the lower half of the BGA 1 are set so that the direction of polarization of the light that passes through each one is orthogonal. That is, when P polarized light passes through polarizing panel 62, the light passing through polarizing panel 63 becomes S polarized light.

Furthermore, on the right side of the BGA 1 is mounted a polarized beam splitter 70 that has a spectral function, which deflects 90° the light polarized by polarizing panel 62 and guides it to camera C, and passes the light polarized by polarizing panel 63 as-is and guides it to camera B.

In this seventh embodiment, similar to the fifth embodiment depicted in FIGS. 5(a) and 5(b) above, light 60 and white fluorescent light 20 are turned on alternately. That is, when light 60 is on, white fluorescent light 20 is off, and when white fluorescent light 20 is on, light 60 is off.

Further, in the case of the embodiment depicted in FIG. 7, a single light bulb 60 was used as the illumination for both polarizing panels 62, 63, but a separate light can also be used for each panel.

Eighth Embodiment

Figure 9:
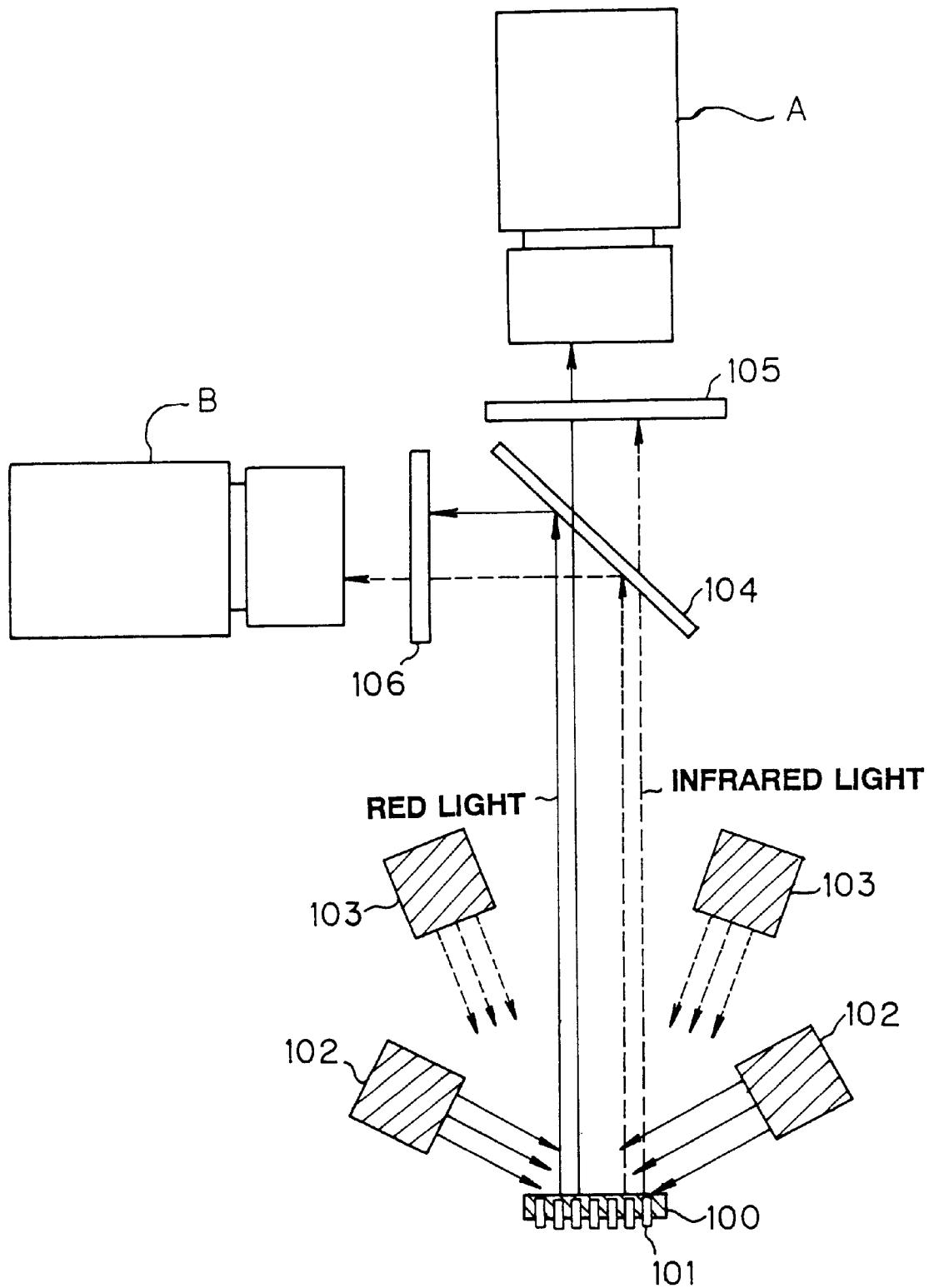
FIG. 9 is a schematic diagram showing an eighth embodiment of the present invention.

FIG. 9 shows an eighth embodiment of the present invention. For this embodiment depicted in FIG. 9, a Small Outline Package (SOP) 100 is used as the semiconductor package for inspection purposes, and inspection of the manufacturing number, manufacturer's name and other markings indicated on the upper surface of this semiconductor package (inspection for missing letters, blurredness and displacement) is carried out simultaneously with inspections for pitch variations and position/direction displacement among the leads 101.

In other words, in FIG. 9, a red LED 102, which is the illumination for inspecting markings, is mounted above the SOP 100, and above that is positioned an infrared LED 103, which is the illumination for inspecting leads. That is, the optimal location for carrying out proper illumination differs for the markings inspection illumination 102 and the lead inspection illumination 103, respectively, and each illumination 102, 103 is positioned in the optimal location for each inspection. Further, if these lights 102, 103 are of different wavelengths, other colors can also be used.

A beam splitter 104 is positioned directly above the SOP 100, and passes a portion of the reflected light from the SOP 100, and deflects the remaining light 90°.

Camera A is for imaging a plan view of the SOP 100, and images an area that includes the markings indicated on the upper surface of the SOP. An infrared filter 105, which blocks infrared light, is mounted directly in front of camera A. Camera B is for imaging a plan view of the SOP for inspecting the leads, and has a visible light filter 106, which blocks visible light, mounted directly in front of it.

That is, in this case, an attempt is made to achieve the functions of the dichroic beam splitter 50 depicted in FIG. 6 above (splitting incident light in accordance with the wavelength of the incident light) via a configuration consisting of a beam splitter 104, an infrared filter 105 and a visible light filter 106. This configuration can be used in place of a dichroic beam splitter 50.

With this configuration shown in FIG. 9, the red LED 102 for inspecting markings, and the infrared LED 103 for inspecting leads are on at the same time when inspecting the SOP 100.

Red light from the red LED 102, after being reflected and scattered by the SOP 100, both passes through and is reflected by the beam splitter 104, and because the reflected light is blocked by the visible light filter 106, it is incident only on camera A.

Meanwhile, infrared light from the infrared LED 103, after being reflected and scattered by the SOP 100, both passes through and is reflected by the beam splitter 104, and because the light that passes through is blocked by the infrared filter 105, it is incident only on camera B.

Thus, in accordance with this embodiment, because the emission wavelength of the light for inspecting lettering varies from that of the light for inspecting leads, and because an optical filter that passes only one of these lights is mounted in front of each camera A, B, respectively, these two lights 102, 103 can be on at the same time, and both cameras A, B can image simultaneously, thus making it possible to speed up the semiconductor package inspection process more than in the past.

Ninth Embodiment

Figure 10:
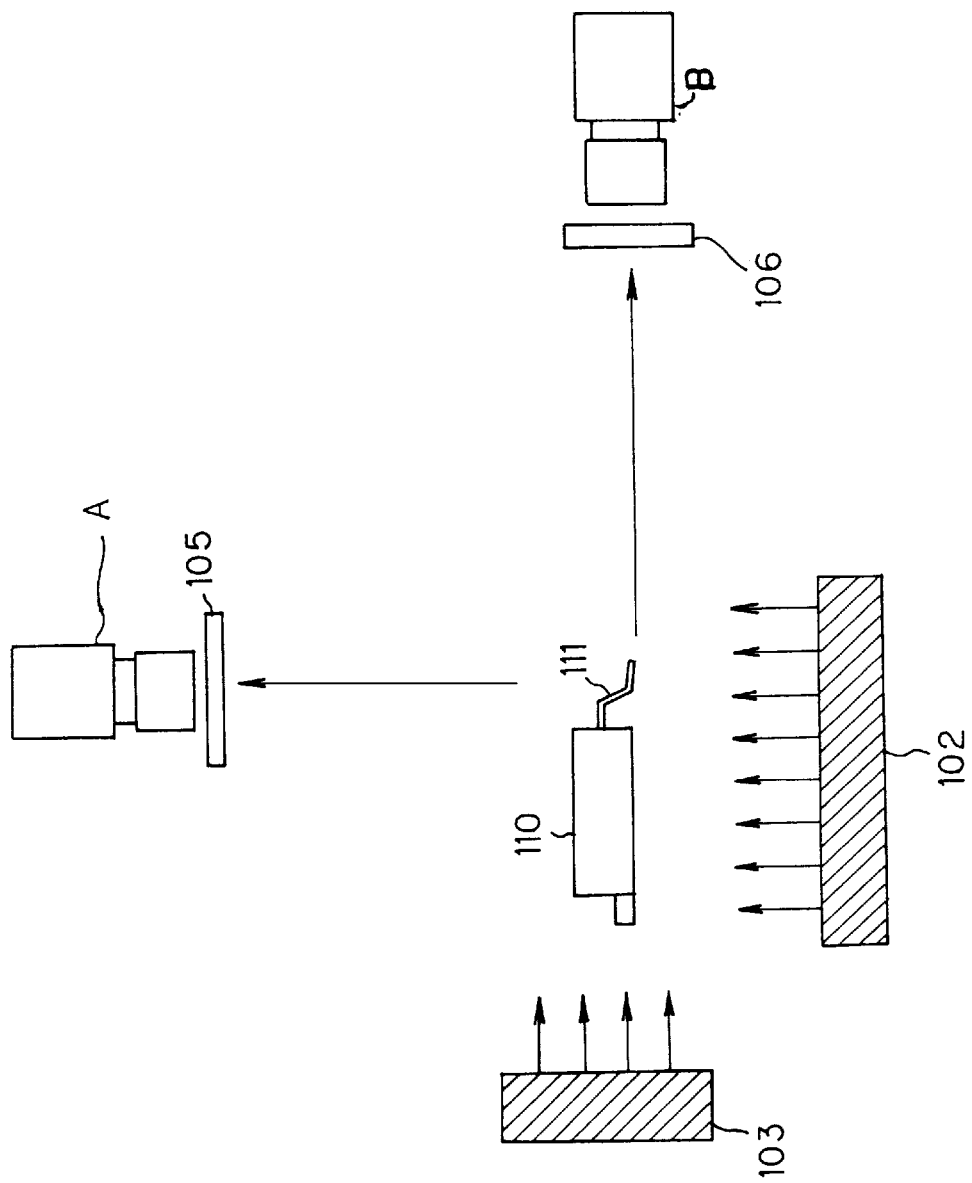
FIG. 10 is a schematic diagram showing a ninth embodiment of the present invention.

FIG. 10 shows a ninth embodiment of the present invention.

With this embodiment, a power transistor 110 is used as the semiconductor package, and the leads 111 of this power transistor 110 are inspected from two different directions.

That is, in FIG. 10, a red LED 102, which is the illumination for camera A, is positioned below the power transistor 110, and this red LED 102 illuminates the power transistor 110 from below using a red light. Further, an infrared LED 103, which is the illumination for camera B, is positioned beside the power transistor 110, and this infrared LED 103 illuminates the power transistor 110 from the side using an infrared light.

Camera A is mounted above the power transistor 110, and images the leads 111 of the power transistor 110 from above. Camera B is set up on the opposite side of the power transistor 110 from the infrared LED 103, and images the leads 111 of the power transistor 110 from the side.

An infrared filter 105, which blocks infrared light, is mounted in front of Camera A, and a red light filter 106, which blocks red light, is mounted in front of Camera B.

FIGS. 11(*a*) and 11(*b*) show examples of images of the power transistor 110 picked up by the cameras A, B.

In this configuration shown in FIG. 10, the red LED 102 and the infrared LED 103 are on at the same time during inspection of the power transistor 110.

The red light from the red LED 102 is both reflected and scattered by the power transistor 110, and is also incident on camera A via the infrared filter 105 as-is without coming in contact with the power transistor 110. Conversely, the red light that is reflected and scattered by the power transistor 110 and heads toward camera B is not incident on camera B because it is blocked by the visible light filter 106.

Further, the infrared light from the infrared LED 103 is both reflected and scattered by the power transistor 110, and is also incident on camera B via the visible light filter 106 as-is without coming in contact with the power transistor 110. Conversely, the infrared light that is reflected and scattered by the power transistor 110 and heads toward camera A is not incident on camera A because it is blocked by the infrared filter 105.

Thus, in accordance with this embodiment, because the emission wavelength of these two lights are varied, and because an optical filter that passes only one of these lights is mounted in front of each camera A, B, respectively, these two lights 102, 103 can be on at the same time, and both cameras A, B can image simultaneously, thus making it possible to speed up the semiconductor package inspection process more than in the past.

Tenth Embodiment

Figure 12:
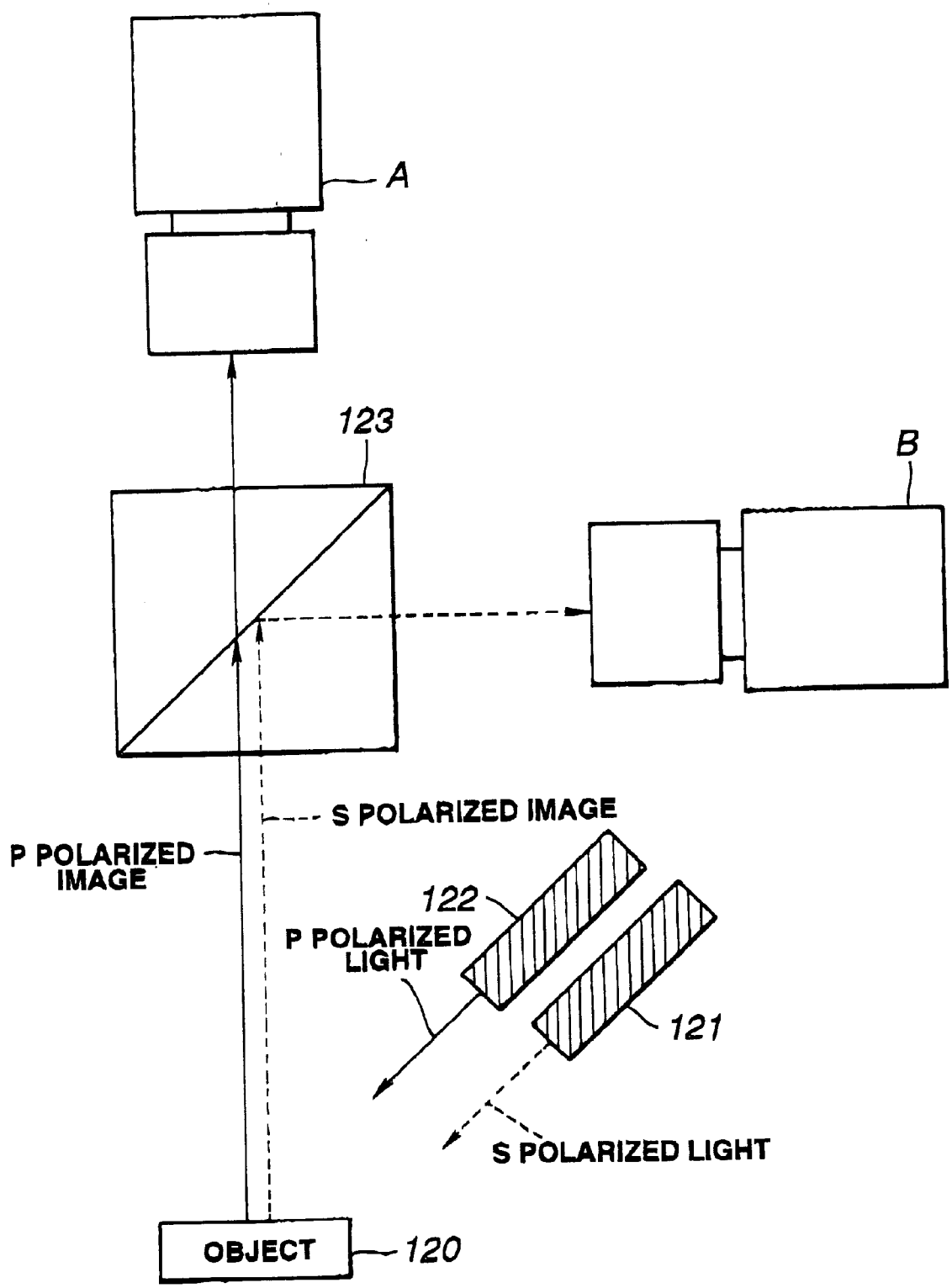
FIG. 12 is a schematic diagram showing a tenth embodiment of the present invention.

FIG. 12 shows a tenth embodiment of the present invention.

This embodiment, similar to the embodiment shown in FIG. 9 above, is applied to situations wherein two different kinds of inspections are performed simultaneously, such as Inspection of IC markings and inspection of leads a. Inspection of IC markings and inspection of IC voids An S polarizing light 121 is the illumination for one type of inspection, and is positioned in the optimum location for that inspection. It generates S polarized light.

A P polarizing light 122 is the illumination for the other type of inspection, and is positioned in the optimum location for that inspection. It generates P polarized light.

A polarized beam splitter 123 separates in accordance with the direction of polarization light from the inspection object illuminated by the S polarizing light 121 and the P polarizing light 122, and reflects the S polarized light while passing the P polarized light.

Camera A is positioned so as to image a picture of the inspection object by virtue of the P polarized light passed by the polarized beam splitter 123, and camera B is positioned so as to image a picture of the inspection object by virtue of the S polarized light reflected by the polarized beam splitter 123.

With the configuration shown in FIG. 12 as well, the P polarizing light 122 and the S polarizing light 121 are on at the same time when the inspection object 120 is being inspected.

The light from the inspection object illuminated by the P polarizing light is incident on camera A after passing through the polarized beam splitter 123. Conversely, the light from the inspection object illuminated by the S polarizing light is incident on camera B after passing through the polarized beam splitter 123.

Thus, in accordance with this embodiment, because the direction of polarization of these two lights is varied, and because the illumination from the inspection object of each of these lights is split in accordance with the direction of polarization and made incident on each camera by a polarized beam splitter 123, these two lights 121, 122 can be on at the same time, and both cameras A, B can image simultaneously, thus making it possible to speed up the semiconductor package inspection process more than in the past.

Eleventh Embodiment

Figure 13:
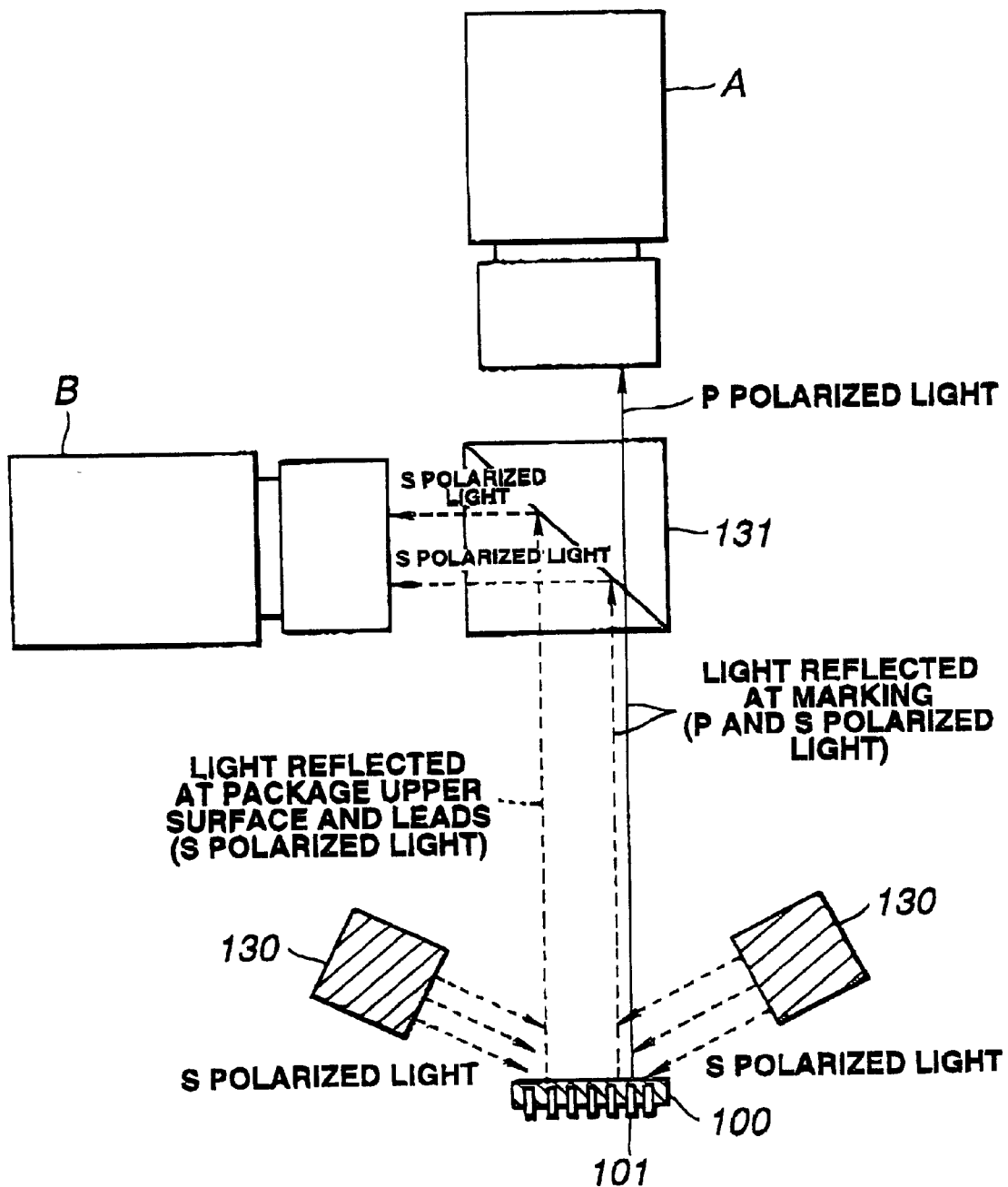
FIG. 13 is a schematic diagram showing an eleventh embodiment of the present invention.

FIG. 13 shows an eleventh embodiment of the present invention.

With the embodiment depicted in FIG. 13, just as with the embodiment depicted in FIG. 9 above, inspection of the manufacturing number, manufacturer's name and other markings indicated on the upper surface of this semiconductor package is carried out simultaneously with inspections for pitch variations and position/direction displacement among the leads.

Figure 14A:
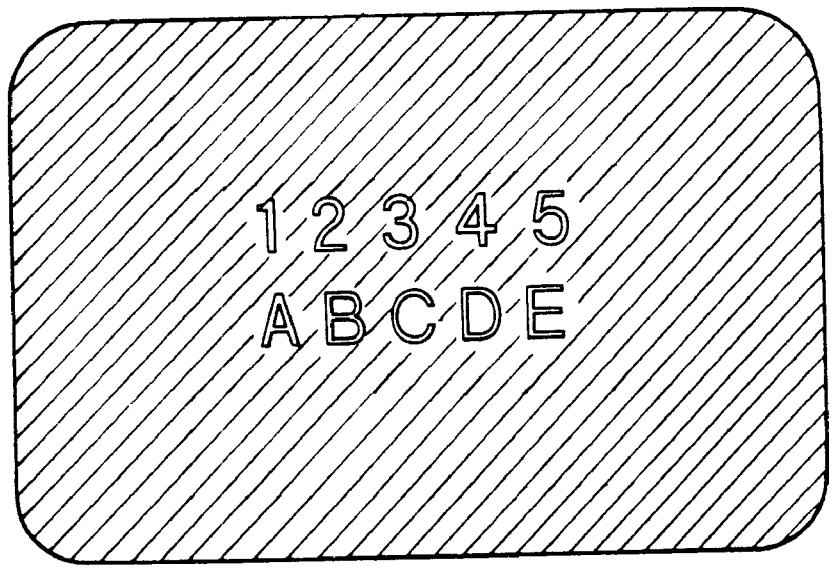
FIGS. 14(a) and 14(b) are schematic diagrams showing ideal images for inspecting letter markings and leads.
Figure 14B:
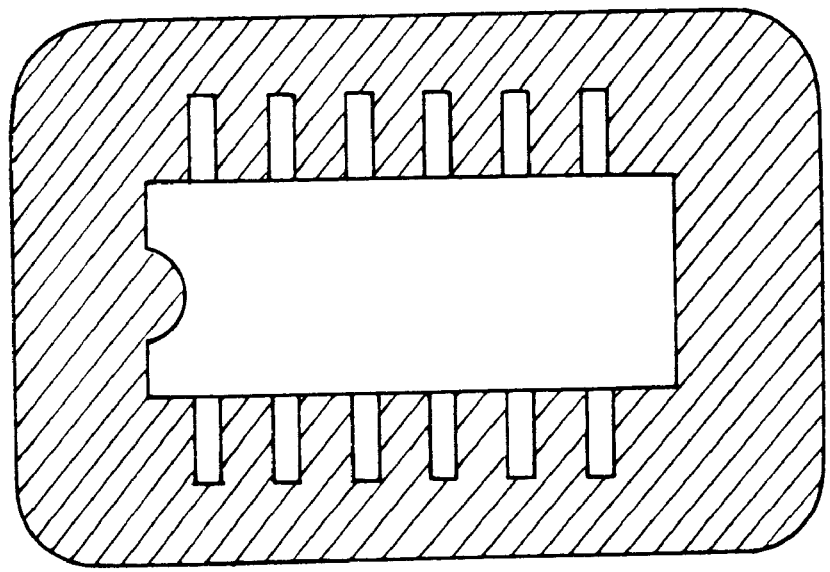

Here, the ideal imaging conditions for inspecting markings comprised of strings of letters indicated on a semiconductor package, as shown in FIG. 14(a), is to make the lettering appear white (that is, increase reflection) and the background appear black (that is, decreased reflection). Conversely, when inspecting leads, just the opposite holds true. As shown in FIG. 14(b), the packages surface and leads should show up as white, while the background shows up as black.

To perform two types of inspection, for which the ideal imaging conditions vary like this, as in the embodiment shown in FIG. 9 above, there is the method whereby two types of illumination with different emission wavelengths is used, in which case, two types of illumination are required.

Accordingly, this eleventh embodiment depicts a method, whereby the above-described two types of inspections can be performed simultaneously and with a high degree of accuracy using only one type of illumination.

In FIG. 13, light 130 illuminates a semiconductor package 100 with a linearly polarized light (in this case, S polarized light).

Since the semiconductor packaging material is nearly black, and its surface is smooth, reflection from the upper surface of the semiconductor package is primarily just surface reflection, diffuse reflection does not occur. Further, because the leads 101 of the semiconductor package are made of metal, the reflection from these leads is also only surface reflection, and diffuse reflection does not occur. In other words, there is no change in the direction of polarization in reflection from the upper surface of the semiconductor package and the leads, and therefore, in this case, the reflected light from these parts becomes S polarized light.

Conversely, the reflection of the markings themselves, which comprise letters and so forth indicated on the upper surface of the package, is diffuse reflection. Consequently, the light reflected from the markings themselves is a mixture of both S-polarized and P-polarized components.

A polarized beam splitter 131, which is mounted above the semiconductor package 100, in this case, is set to pass P polarized light, and to deflect 90° S polarized light.

Therefore, only P polarized light is incident on camera A, and only S polarized light is incident on camera B.

That is, the light reflected from the markings comprises P polarized light and S polarized light, and the light reflected from the upper surface of the semiconductor package and the leads comprises S polarized light. Since the polarized beam splitter 131 only passes S polarized light on to camera B, and only passes P polarized light on to camera A, only reflected light corresponding to the markings is incident on camera A. That is, in a camera A photographed image, only an image that corresponds to the markings themselves shows up bright, and everything else is dark.

Conversely, with camera B, it is possible to obtain a photographed image, wherein the image of the upper surface of the semiconductor package, including the markings, and the image of the leads show up bright, and other background portions are dark.

Thus, with this embodiment, when used for markings and lead inspections, it is possible to simultaneously obtain two types of photographed images of nearly ideal imaging conditions approaching those shown in FIGS. 14(a) and 14(b).

Further, images photographed with camera B can also be used to inspect for voids and other defects in the surface of a semiconductor package.

Twelfth Embodiment

Figure 15A:
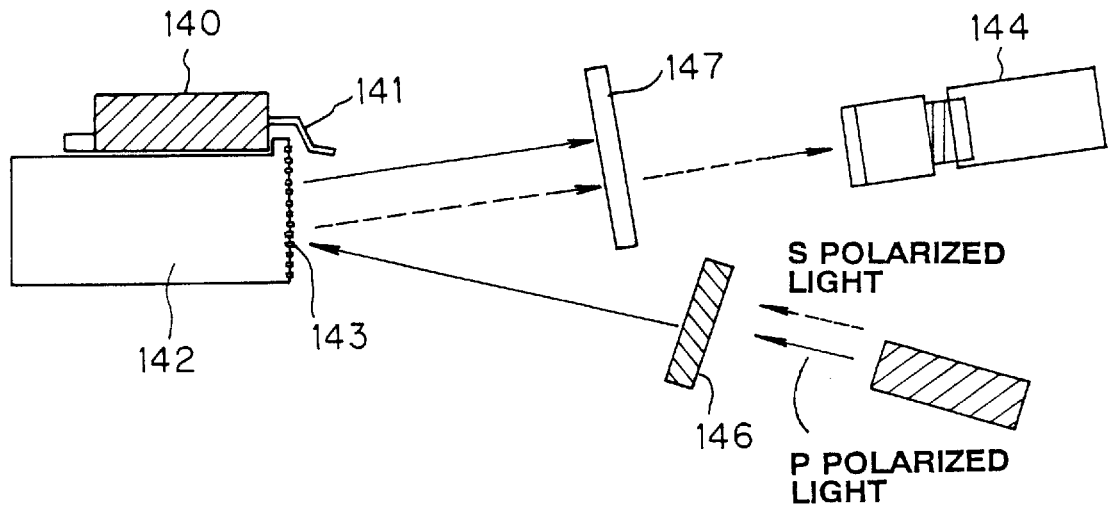
FIGS. 15(a) and 15(b) are schematic diagrams showing a twelfth embodiment of the present invention.
Figure 15B:
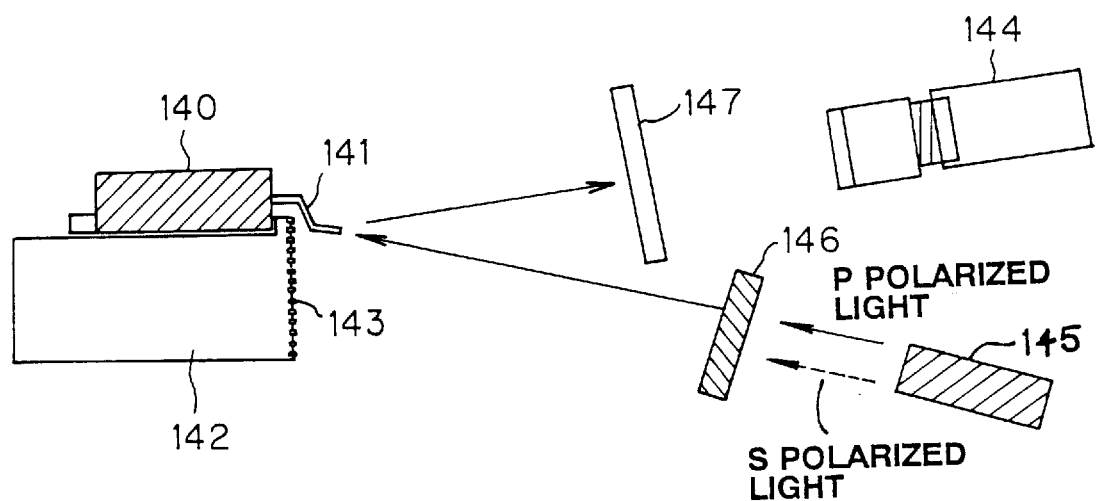

FIGS. 15(a) and 15(b) show a twelfth embodiment of the present invention.

This twelfth embodiment provides a method for obtaining illumination equivalent to the backlight illumination applied to semiconductor package inspection.

The illumination most often applied to the inspection of semiconductor packages is backlighting. However, there are numerous cases, in which it is impossible to position a light source behind the object to be inspected due to the limited space on the production line.

Accordingly, with this embodiment, backlight illumination is achieved without positioning a light source behind the inspection object.

In FIGS. 15(a) and 15(b), a power transistor 140, which is the inspection object, is placed on an inspection table 142, and in this case, the inspection object 140 is imaged from the side by camera 144. Therefore, either a surface coating 143 is applied to the side of the inspection table 142, which becomes the background of the inspection object in the imaging screen, so as to achieve either diffuse reflection or absorbed reflection, or a member that exhibits this kind of reflection is affixed to the side of the inspection table 142.

It is desirable to use an opalescent acrylic resin as the surface coating to achieve diffuse reflection or absorbed reflection.

A P polarizing filter 146 is positioned in front of a light 145, and only P polarized light are irradiated in the direction of the inspection object 140.

Here, as described above, the reflection from the power transistor package substrate 140 and the metal leads 141 is primarily just surface reflection, and diffuse reflection does not occur. That is, the direction of polarization of the illuminated light reflected from a side of the package substrate and the leads 141 does not change, and therefore, the reflected light from these parts, in this case, becomes P polarized light (See FIG. 15(b)).

Conversely, because a surface coating 143, which causes diffuse reflection or absorbed reflection, is applied to a side of the inspection table 142, both S polarized light and P polarized light components are intermixed in the light reflected from this background part (See FIG. 15(a)).

Because a polarizing filter 147, which is positioned in front of a camera 144, is set so as to pass S polarized light, only S polarized light is incident on the camera 144.

Figure 16:
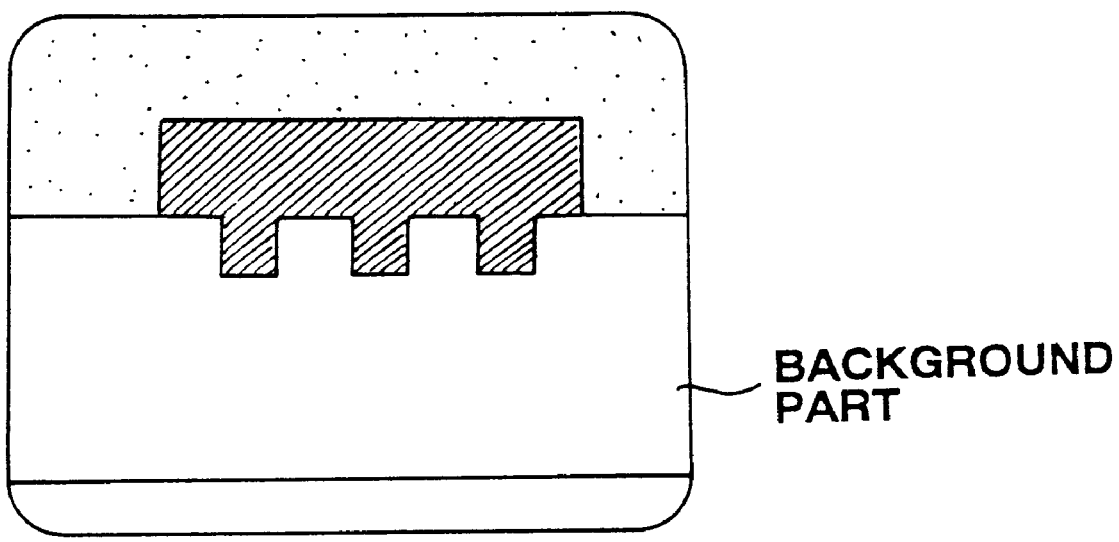
FIG. 16 is a schematic diagram showing an example of an image picked up using the twelfth embodiment of the present invention.

That is, reflected light from the package substrate 140 and metal leads 141 comprises only P polarized light, and reflected light from the side of the inspection table, which is the background part, comprises P polarized light and S polarized light. Because the polarizing filter 147 only passes S polarized light on to the camera 144, only the light reflected from the inspection table, which is the background part, is incident on the camera 144. Therefore, as shown in FIG. 16, in the image photographed by camera 144, only the side of the inspection table, which is this background part, shows up bright, and the package substrates 140 and metal leads 141 are dark.

Thus, with this embodiment, it is possible to achieve a photographed image, in which the metal leads and package substrate part are dark images, and the background thereto appears bright. This makes it possible to achieve images that are practically equivalent to when backlighting is used, without using backlight illumination.

Further, when imaging a semiconductor package from above, the upper surface of the inspection table can be coated to achieve diffuse reflection.

Although the present invention was applied to BGA and SOP in the above-described embodiments, it can also be applied arbitrarily to the inspection of terminals on other semiconductor packages, such as a Dual Inline Package (DIP), Small Outline J-leaded Package (SIJ), Pin Grid Array (PGA), Quad Flat Package (QFP) and Quad Flat J-leaded Package (QFJ). The present invention can also be applied to the inspection of connectors and other electrode arrays. Furthermore, the present invention can also be applied to the inspection of IC terminal flatness (inspection of IC terminal displacement in the up-down direction), and bonding wire height inspection.

What is claimed is:

1. A semiconductor package inspection apparatus, comprising:
    oblique imaging means which images a package surface of a semiconductor package from an oblique direction at a prescribed angle of elevation;
    plan view imaging means which images a plan view image of the package surface of the semiconductor package;
    oblique imaging illumination means which illuminates the package surface for imaging by the oblique imaging means; and
    plan view imaging illumination means which illuminates the package surface for imaging by the plan view imaging means,
    whereby terminals of the semiconductor package are inspected based on image data of the oblique imaging means and the plan view imaging means,
    the inspection apparatus being characterized in that emission spectrum characteristics of the oblique imaging illumination means and plan view imaging illumination means are different from each other, and the inspection apparatus further comprises:
        first filter means which is provided on the optical path from the semiconductor package to the oblique imaging means, and which passes light from the oblique imaging illumination means, and blocks light from the plan view imaging illumination means;
        second filter means which is provided on the optical path from the semiconductor package to the plan view imaging means, and which passes light from the plan view imaging illumination means, and blocks light from the oblique imaging illumination means; and
        control means which simultaneously turns on the oblique imaging and plan view imaging illumination means, and inspects the terminals of the semiconductor package based on image data of the oblique imaging means and plan view imaging means.

2. The semiconductor package inspection apparatus according to claim 1, wherein the colors of the oblique imaging and plan view imaging illumination means are different from each other.

3. The semiconductor package inspection apparatus according to claim 2, wherein the plan view imaging illumination means is a ring-shaped fluorescent light positioned around the semiconductor package.

4. A semiconductor package inspection apparatus, comprising:
    oblique imaging means which images a package surface of a semiconductor package from an oblique direction at a prescribed angle of elevation;
    plan view imaging means which images a plan view image of the package surface of the semiconductor package;
    oblique imaging illumination means which illuminates the package surface for imaging by the oblique imaging means; and
    plan view imaging illumination means which illuminates the package surface for imaging by the plan view imaging means,
    whereby terminals of the semiconductor package are inspected based on image data of the oblique imaging means and the plan view imaging means,
    the semiconductor package inspection apparatus being characterized in that polarization characteristics of the oblique imaging illumination means and plan view imaging illumination means are different from each other, and the semiconductor package inspection apparatus further comprises:
        first polarizing filter means which is provided on the optical path from the semiconductor package to the oblique imaging means, and which passes light from the oblique imaging illumination means, and blocks light from the plan view imaging illumination means;
        second polarizing filter means which is provided on the optical path from the semiconductor package to the plan view imaging means, and which passes light from the plan view imaging illumination means, and blocks light from the oblique imaging illumination means; and
        control means which simultaneously turns on the oblique imaging and plan view imaging illumination means, and inspects terminals of the semiconductor package based on image data of the oblique imaging means and plan view imaging means.

5. A semiconductor package inspection apparatus, comprising:

oblique imaging means which images a package surface of a semiconductor package from an oblique direction at a prescribed angle of elevation;

plan view imaging means which images a plan view image of the package surface of the semiconductor package;

oblique imaging illumination means which illuminates the package surface for imaging by the oblique imaging means; and plan view imaging illumination means which illuminates the package surface for imaging by the plan view imaging means, whereby terminals of the semiconductor package are inspected based on image data of the oblique imaging means and the plan view imaging means, the semiconductor package inspection apparatus being characterized in that the oblique imaging means comprises a first oblique imaging means which is positioned on one side of the semiconductor package, and a second oblique imaging means which is positioned on the opposite side of the semiconductor package from this first oblique imaging means, and these first and second oblique imaging means are positioned by shifting the optical axis of each imaging means so that a different area of the semiconductor package is imaged by each; and the oblique imaging illumination means comprises a first oblique imaging illumination means which illuminates the package surface for imaging by the first oblique imaging means, and a second oblique imaging illumination means which illuminates the package surface for imaging by the second oblique imaging means, and the respective emission spectrum characteristics of these first and second oblique imaging illumination means and the plan view imaging illumination means are different from each other, and the inspection apparatus further comprises:

first filter means which is provided on the optical path from the semiconductor package to the first oblique imaging means, and which passes light from the first oblique imaging illumination means, and blocks light from the plan view imaging illumination means and the second oblique imaging illumination means;

second filter means which is provided on the optical path from the semiconductor package to the second oblique imaging means, and which passes light from the second oblique imaging illumination means, and blocks light from the first oblique imaging illumination means and the plan view imaging illumination means;

third filter means which is provided on the optical path from the semiconductor package to the plan view imaging means, and which passes light from the plan view imaging illumination means, and blocks light from the first and second oblique imaging illumination means; and control means which simultaneously turns on the first and second oblique imaging illumination means and the plan view imaging illumination means, and inspects the terminals of the semiconductor package based on image data of the first and second oblique imaging means and plan view imaging means.

6. A semiconductor package inspection apparatus, comprising:

oblique imaging means which images a package surface of a semiconductor package from an oblique direction at a prescribed angle of elevation;

plan view imaging means which images a plan view image of the package surface of the semiconductor package;

oblique imaging illumination means which illuminates the package surface for imaging by the oblique imaging means; and plan view imaging illumination means which illuminates the package surface for imaging by the plan view imaging means, whereby terminals of the semiconductor package are inspected based on image data of these oblique imaging means and plan view imaging means;

the inspection apparatus being characterized in that the oblique imaging means comprises a first oblique imaging means which is positioned on one side of the semiconductor package, and a second oblique imaging means which is positioned on the opposite side of the semiconductor package from this first oblique imaging means, and these first and second oblique imaging means are positioned by shifting the optical axis of each imaging means so that a different area of the semiconductor package is imaged by each; and the oblique imaging illumination means comprises a first oblique imaging illumination means which illuminates the package surface for imaging by the first oblique imaging means, and a second oblique imaging illumination means which illuminates the package surface for imaging by the second oblique imaging means, and the respective polarization characteristics of these first and second oblique imaging illumination means are varied, and the inspection apparatus further comprises a first polarizing filter means which is provided on the optical path from the semiconductor package to the first oblique imaging means, and which passes light from the first oblique imaging illumination means, and blocks light from the second oblique imaging illumination means;

second polarizing filter means which is provided on the optical path from the semiconductor package to the second oblique imaging means, and which passes light from the second oblique imaging illumination means, and blocks light from the first oblique imaging illumination means; and control means which turns on the first and second oblique imaging illumination means at the same time, controls each of the illumination means so that these first and second oblique imaging illumination means and the plan view imaging illumination means are on alternately, and inspects terminals of the semiconductor package based on image data of the first and second oblique imaging means and plan view imaging means.

7. The semiconductor package inspection apparatus according to claim 5, wherein the plan view imaging illumination means is a ring-shaped fluorescent light positioned around the semiconductor package.

8. A semiconductor package inspection apparatus, comprising:

oblique imaging means which images a package surface of semiconductor package from an oblique direction at a prescribed angle of elevation;

plan view imaging means which images a plan view image of the package surface of the semiconductor package;

oblique imaging illumination means which illuminates the package surface for imaging by the oblique imaging means;

plan view imaging illumination means which illuminates the package surface for imaging by the plan view imaging means, whereby terminals of the semiconductor package are inspected based on image data of these oblique imaging means and plan view imaging means, the inspection apparatus being characterized in that the oblique imaging means comprises a first oblique imaging means which is positioned on one side of the semiconductor package, and a second oblique imaging means which is positioned on the same side of the semiconductor package as this first oblique imaging means, and the optical axis of each imaging means is set so that these first and second oblique imaging means each image a different area of the semiconductor package; and the oblique imaging illumination means comprises a first oblique imaging illumination means which illuminates the package surface for imaging by the first oblique imaging means, and a second oblique imaging illumination means which illuminates the package surface for imaging by the second oblique imaging means, and the respective emission spectrum characteristics of these first and second oblique imaging illumination means and the plan view imaging illumination means are varied; and it is further characterized in that it comprises:

a dichroic beam splitter which is provided on the optical path from the semiconductor package to the first and second oblique imaging means, and which splits incident light so as to guide the light of the first oblique imaging illumination means to the first oblique imaging means, and to guide the light of the second oblique imaging illumination means to the second oblique imaging means;

filter means which is provided on the optical path from the semiconductor package to the plan view imaging means, and which passes light from the plan view imaging illumination means, and blocks light from the first and second oblique imaging illumination means; and control means which simultaneously turns on the first an second oblique imaging illumination means and the plan view imaging illumination means, and inspects terminals of the semiconductor package based on image data of the first and second oblique imaging means and plan view imaging means.

9. A semiconductor package inspection apparatus, comprising:

oblique imaging means which images a package surface of a semiconductor package from an oblique direction at a prescribed angle of elevation;

plan view imaging means which images a plan view image of the package surface of the semiconductor package;

oblique imaging illumination means which illuminates the package surface for imaging by the oblique imaging means; and plan view imaging illumination means which illuminates the package surface for imaging by the plan view imaging means, whereby terminals of the semiconductor package are inspected based on image data of these oblique imaging means and plan view imaging means;

the inspection apparatus being characterized in that the oblique imaging means comprises a first oblique imaging means which is positioned on one side of the semiconductor package, and a second oblique imaging means which is positioned on the same side of the semiconductor packages as this first oblique imaging means, and the optical axis of each imaging means is set so that these first and second oblique imaging means each image a different area of the semiconductor package; and the oblique imaging illumination means comprises a first oblique imaging illumination means which illuminates the package surface for imaging by the first oblique imaging means, and a second oblique imaging illumination means which illuminates the package surface for imaging by the second oblique imaging means, and the respective polarization characteristics of these first and second oblique imaging illumination means are varied, and the inspection apparatus further comprises a polarized beam splitter which is provided on the optical path from the semiconductor package to the first and second oblique imaging means, and which splits incident light so as to guide the light from the first oblique imaging illumination means to the first oblique imaging means, and to guide the light from the second oblique imaging illumination means to the second oblique imaging means; and control means which simultaneously turns on the first and second oblique imaging illumination means, controls each of the illumination means so that these first and second oblique imaging illumination means and the plan view imaging illumination means are on alternately, and inspects terminals of the semiconductor package based on image data of the first and second oblique imaging means and plan view imaging means.

10. The semiconductor package inspection apparatus according to claim 8, wherein the plan view imaging illumination means is a ring-shaped fluorescent light positioned around the semiconductor package.

11. A semiconductor package inspection apparatus, comprising:

first imaging means which images a package surface of a semiconductor package from a first direction;

second imaging device which images the package surface of a the semiconductor package from a second direction that differs from the first direction;

first illumination means which illuminates the package surface for imaging by the first imaging means; and second illumination means which illuminates the package surface for imaging by the second imaging means, whereby the semiconductor package is inspected using these first and second image data, the inspection apparatus being characterized in that emission wavelength characteristics of the first and second illumination means are different from each other, and the inspection apparatus further comprises:

first filter means which is provided on the optical path from the semiconductor package to the first imaging means, and which passes light from the first illumination means, and blocks light from the second illumination means;

second filter means which is provided on the optical path from the semiconductor package to the second imaging means, and which passes light from the second illumination means, and blocks light from the first illumination means; and control means which simultaneously turns on the first an second illumination means, and inspects the semiconductor package based on image data of the first and second imaging means.

12. The semiconductor package inspection apparatus according to claim 11, wherein the first and second imaging means are positioned so that a portion of the imaging optical axis from the semiconductor package to the first imaging means, and a portion of the imaging optical axis from the semiconductor package to the second imaging means become integrated, and the inspection apparatus further comprises:

a beam splitter which is positioned on these integrated imaging optical axes, and which splits the first and second semiconductor package images illuminated respectively by the first and second lights which have different wavelength characteristics, and guides these images to the first and second imaging means.

13. The semiconductor package inspection apparatus according to claim 12, wherein the beam splitter, and the first and second filter means comprises a dichroic beam splitter, respectively.

14. A semiconductor package inspection apparatus, comprising:

first imaging means which images a package surface of a semiconductor package from a first direction;

second imaging device which images the package surface of the semiconductor package from a second direction that differs from the first direction;

first illumination means which illuminates the package surface for imaging by the first imaging means; and second illumination means surface illuminates the package surface for imaging by the second imaging means, whereby the semiconductor package is inspected using these first and second image data, the inspection apparatus being characterized in that polarization characteristics of the first and second illumination means are different from each other, and the inspection apparatus further comprises:

first polarizing filter means which is provided on the optical path from the semiconductor package to the first imaging means, and which passes light from the first illumination means, and blocks light from the second illumination means;

second polarizing filter means which is provided on the optical path from the semiconductor package to the second imaging means, and which passes light from the second illumination means, and blocks light from the first illumination means; and control means which simultaneously turns on the first and second illumination means, and inspects the semiconductor package based on image data of the first, and second imaging means.

15. The semiconductor package inspection apparatus according to claim 14, wherein the first and second imaging means are positioned so that a portion of the imaging optical axis from the semiconductor package to the first imaging means, and a portion of the imaging optical axis from the semiconductor package to the second imaging means become integrated, and the inspection apparatus further comprises a beam splitter which is positioned on these integrated imaging optical axes, and which splits the first and second semiconductor package images illuminated respectively by the first and second lights which have different wavelength characteristics, and guides these images to the first and second imaging means.

16. A semiconductor package inspection apparatus having an imaging device for imaging an area including an upper surface of a semiconductor package which is provided with a plurality of metal terminals, for inspecting markings indicated onto the upper surface of the semiconductor package as well as the semiconductor package and the metal terminals based on image data from the imaging device, comprising:

illumination means which illuminates the area including the upper surface of the semiconductor package using linearly polarized light with a prescribed direction of polarization;

a polarized beam splitter which is provided above the semiconductor package, and which splits into respectively different directions linearly polarized light with a direction of polarization coinciding with linearly polarized light from the illumination means and linearly polarized light with a direction of polarization being orthogonal to linearly polarized light from the illumination means, within the illuminated light from the illumination means reflected by the semiconductor package;

first imaging means which is provided on one of the optical paths split by the polarized beam splitter, and on which is incident the linearly polarized light with a direction of polarization coinciding with the linearly polarized light from the illumination means;

second imaging means which is provided on the other optical path split by the polarized beam splitter, and on which is incident the linearly polarized light with a direction of polarization being orthogonal to the linearly polarized lights from the illumination means; and control means which inspects the semiconductor package and metal terminals based on image date from the first imagine means, and inspects markings indicated on the upper surface of the semiconductor package based on image data from the second imaging means.

17. A semiconductor package inspection apparatus having an imaging device for imaging a semiconductor package which is provided with a plurality of metal terminals and is placed on an inspection table, for inspecting the metal terminals based on image data from the imaging device, the inspection apparatus being characterized in that surface of the inspection table which serves as a background to the metal terminals within a field of view region of the imaging device, exhibits diffuse reflection or absorption reflection properties, and the inspection apparatus further comprises:

illumination means which emits a linearly polarized light with a prescribed direction of polarization to illuminate the field of view region of the imaging device; and polarizing filter means which is provided between the imaging device and the semiconductor package, and which only passes polarized light with a direction of polarization being orthogonal to the linearly polarized light from the illumination means.

18. The semiconductor package inspection apparatus according to claim 6, wherein the plan view imaging illumination means is a ring-shaped fluorescent light positioned around the semiconductor package.

19. The semiconductor package inspection apparatus according to claim 9, wherein the plan view imaging illumination means is a ring-shaped fluorescent light positioned around the semiconductor package.

* * * * *